(12) United States Patent
Klapproth et al.

(10) Patent No.: US 12,102,973 B2
(45) Date of Patent: *Oct. 1, 2024

(54) THREE-DIMENSIONAL POLYMER NETWORKS WITH CHANNELS SITUATED THEREIN

(71) Applicant: SAFEGUARD BIOSYSTEMS HOLDINGS LTD., London (GB)

(72) Inventors: Holger Klapproth, Freiburg (DE); Sonja Bednar, Gundelfingen (DE)

(73) Assignee: Safeguard Biosystems Holdings Ltd., London (GB)

( * ) Notice: Subject to any disclaimer, the term of this patent is extended or adjusted under 35 U.S.C. 154(b) by 69 days.

This patent is subject to a terminal disclaimer.

(21) Appl. No.: 17/866,080

(22) Filed: Jul. 15, 2022

(65) Prior Publication Data

US 2023/0141219 A1 May 11, 2023

Related U.S. Application Data

(63) Continuation of application No. 16/062,761, filed as application No. PCT/EP2016/081457 on Dec. 16, (Continued)

(30) Foreign Application Priority Data

Dec. 18, 2015 (EP) ..................................... 15201355

(51) Int. Cl.
*B01J 19/00* (2006.01)
*C12Q 1/6837* (2018.01)
*C12Q 1/689* (2018.01)

(52) U.S. Cl.
CPC ........ *B01J 19/0046* (2013.01); *C12Q 1/6837* (2013.01); *C12Q 1/689* (2013.01); (Continued)

(58) Field of Classification Search
None
See application file for complete search history.

(56) References Cited

U.S. PATENT DOCUMENTS 4,196,070 A 4/1980 Chao et al.
9,738,926 B2 8/2017 Klapproth et al.
(Continued)

FOREIGN PATENT DOCUMENTS

CN 1033126 5/1989
CN 1297042 5/2001
(Continued)

OTHER PUBLICATIONS

Germashev et al., 2019 "Analysis of Fuzzy Data for the Selection of Ingredients of the Polymer Composition" 1-2, pp. 27-30.
(Continued)

*Primary Examiner* — Robert T. Crow
(74) *Attorney, Agent, or Firm* — Biospark Intellectual Property Law

(57) ABSTRACT

The disclosure provides three-dimensional crosslinked polymer networks comprising one or more channels extending from the surface and/or near the surface of the network into the interior of the network, arrays comprising the networks, processes for making the networks, and uses of the networks and arrays.

21 Claims, 11 Drawing Sheets

Related U.S. Application Data 2016, now Pat. No. 11,420,174, which is a continuation-in-part of application No. 15/008,728, filed on Jan. 28, 2016, now Pat. No. 9,738,926.

(52) U.S. Cl.
CPC ............... *B01J 2219/0061* (2013.01); *B01J 2219/00626* (2013.01); *B01J 2219/00644* (2013.01); *B01J 2219/00664* (2013.01)

(56) References Cited

U.S. PATENT DOCUMENTS

| | | | |
|---|---|---|---|
| 9,914,961 | B2 | 3/2018 | Klapproth et al. |
| 10,273,336 | B2* | 4/2019 | Klapproth ......... G01N 33/54366 |
| 11,046,820 | B2 | 6/2021 | Klapproth et al. |
| 2003/0006143 | A1 | 1/2003 | Banerjee et al. |
| 2004/0014083 | A1 | 1/2004 | Yuan et al. |
| 2004/0053298 | A1 | 3/2004 | Mirzabekov et al. |
| 2004/0108992 | A1 | 10/2004 | Rosenberg |
| 2005/0042363 | A1 | 2/2005 | Kukhtin et al. |
| 2005/0123581 | A1* | 6/2005 | Ringeisen ............ A61L 27/502 264/172.11 |
| 2005/0202396 | A1 | 9/2005 | Ruhe |
| 2005/0227241 | A1* | 10/2005 | Fang .................... B01L 3/5085 435/7.1 |
| 2006/0257560 | A1 | 11/2006 | Barone et al. |
| 2008/0176757 | A1 | 7/2008 | Hassibi et al. |
| 2008/0293592 | A1 | 11/2008 | Ruhe et al. |
| 2009/0042741 | A1 | 2/2009 | Northen et al. |
| 2009/0215649 | A1 | 8/2009 | Stuelpnagel et al. |
| 2011/0008442 | A1 | 1/2011 | Zawko et al. |
| 2011/0098414 | A1 | 4/2011 | Fujita et al. |
| 2014/0178455 | A1* | 6/2014 | Nukavarapu .......... A61L 27/18 521/182 |
| 2015/0132565 | A1 | 5/2015 | Mckay et al. |
| 2018/0362719 | A1 | 12/2018 | Klapproth et al. |
| 2019/0211159 | A1 | 7/2019 | Klapproth et al. |
| 2020/0261880 | A1 | 8/2020 | Klapproth et al. |

FOREIGN PATENT DOCUMENTS

| | | |
|---|---|---|
| CN | 1875113 | 12/2006 |
| CN | 101410559 | 4/2009 |
| CN | 103547582 | 1/2014 |
| CN | 104725623 | 6/2015 |
| CN | 104745192 A | 7/2015 |
| CN | 106380621 | 2/2017 |
| EP | 0128953 | 12/1984 |
| EP | 1937327 B1 | 7/2008 |
| EP | 3181700 A1 | 6/2017 |
| JP | 2013034138 | 2/2013 |
| WO | 2005/108992 | 11/2005 |
| WO | 2007/007052 A2 | 1/2007 |
| WO | 2017/103128 A1 | 6/2017 |
| WO | 2018/234253 A1 | 12/2018 |

OTHER PUBLICATIONS

Chen et al., 2001, "Solvo-thermal synthesis of metal chalcogenides and its employment," Chinese Journal of Material Research 2:151-158.

Du et al., 2009, "Synthesis and crystal structure of 4,5-dinitroethylthio-1,3-dithiocyclopenten-2-thione and its Ag(I) complex," Journal of Synthetic Crystals 3(1):39-43.

First Office Action issued Mar. 3, 2023 in CN 201880040927.4.

Extended European Search Report and Opinion issued Mar. 15, 2016 in EP 15201355.3.

International Search Report issued Apr. 12, 2017 in PCT/EP2016/081457.

Written Opinion of the International Searching Authority issued Apr. 12, 2017 in PCT/EP2016/081457.

Arrua et al., 2009, "Macroporous Monolithic Polymers: Preparation and Applications," Materials 2:2429-2466.

Glotov et al., 2015, "Detection of human genome mutations associated with pregnancy complications using 3-D microarray based on macroporous polymer monoliths," Talanta 147:537-546 (abstract only).

Horak et al., 2008, "Superporous poly(2-hydroxyethyl methacrylate) based scaffolds: Preparation and characterization," Polymer 49:2046-2054.

Jerabek et al., 1992, "Accessibility of the Gel Phase in Macroporous Network Polymers: A Comparison of the Fluorescence Probe and Inverse Steric Exclusion Chromatography Techniques," Journal of Polymer Science: Part A: Polymer Chemistry 30:605-611.

Nakayama et al., 1995, "Design and Properties of Photocurable Electroconductive Polymers for Use in Biosensors," ASAIO Journal 41(3):M418-M421.

Matsuda et al., (ASAIO Journal 41 (1995) Jul./Sep. No. 3 (pp. M418-M421).

Murphy et al., 1992, "Synthetic Hydrogels: Part 9—Preparation and Characterisation of Macroporous Hydrophilic Matrices," J. Mater. Chem. 2(10):1007-1013.

Okay, 2000, "Macroporous copolymer networks," Prog. Polym. Sci. 25:711-779.

Oxley et al., 1993, "Macroporous hydrogels for biomedical applications: methodology and morphology," Biomaterials 14(14):1064-1072.

Rendl et al., 2011, "Simple One-Step Process for Immobilization of Biomolecules on Polymer Substrates Based on Surface-Attached Polymer Networks," Langmuir 27:6116-6123.

Extended European Search Report and Opinion issued Oct. 12, 2017 in EP 15201355.3.

International Search Report issued Jul. 5, 2018 in PCT/EP2018/066148.

Amhed, 2015, "Hydrogel: Preparation, characterization, and applications: A review," Journal of Advanced Research, 6:105-121.

Baader et al., 2011, "Polysaccharide microarrays with a CMOS based signal detection unit" Biosensors and Bioelectronics 26(5): 1839-1846.

Tanaka, 1980, "Gels," Scientific American, 244 (1): 124-138.

Zawko et al., 2010 "Crystal templating dendritic pore networks and fibrillar microstructure into hydrogels" Acta Biomaterialia, vol. 6 p. 2415-2421.

Zuev et al., 2010 "Physics and Chemistry of Polymers" Textbook, p. 7.

\* cited by examiner

| Spot ID | Example of the Invention | | Polymer Network without Channels | |
|---|---|---|---|---|
| | Mean | SEM | Mean | SEM |
| LL | 0,0639 | 0,0010 | 0,0623 | 0,0009 |
| GN | 0,0926 | 0,0013 | 0,0701 | 0,0045 |
| GP | 0,0017 | 0,0001 | 0,0011 | 0,0001 |
| S.Aure_1 | 0,0027 | 0,0001 | 0,0021 | 0,0001 |
| S.Aure_2 | 0,0021 | 0,0001 | 0,0014 | 0,0001 |
| E.coli_1 | 0,0623 | 0,0014 | 0,0464 | 0,0058 |
| E.coli_2 | 0,0571 | 0,0010 | 0,0398 | 0,0048 |

Fig. 14

THREE-DIMENSIONAL POLYMER NETWORKS WITH CHANNELS SITUATED THEREIN

1. CROSS REFERENCE TO RELATED APPLICATIONS

This application is a continuation of U.S. application Ser. No. 16/062,761, now U.S. Pat. No. 11,420,174, issued Aug. 23, 2022, which is a national stage application of international application no. PCT/EP2016/081457, filed Dec. 16, 2016, which claims priority under 35 U.S.C. § 119 to European application no. 15201355, filed Dec. 18, 2015 and to U.S. application Ser. No. 15/008,728, filed Jan. 28, 2016, the contents of each of which are incorporated herein in their entireties by reference thereto.

2. BACKGROUND

U.S. Publication No. 2008/0293592 describes a method for covalently immobilizing probe-biomolecules on organic surfaces by means of photoreactive crosslinking agents. The method has in practice proven to be advantageous particularly because it permits an immobilization of probe biomolecules on unreactive surfaces, such as silanized glass supports and substrates made of standard commercial plastics. A polymer is used in the method described in US 2008/0293592 to form a type of three-dimensional network onto which the probe biomolecules can be bonded, either at the network's surface or in the inside of the network. Compared to an organic surface on which the probe biomolecules are only immobilized in two-dimensional form, the three-dimensional immobilization of the biomolecules in the polymer and/or copolymer network permits a higher density of the probe biomolecules on the organic surface. This increases the amount of analyte which can be bonded per surface unit of the organic surface. Use of the surface as biological sensor thus gives rise to a higher measurement accuracy and a high measurement dynamic.

However, a disadvantage of the methods and polymer networks described in U.S. 2008/0293592 is that analyte molecules or analyte components which bind to probe biomolecules arranged on or close to the surface of the polymer network can block the network. Further analyte molecules or analyte constituents can then no longer bind as well to as yet unbound probe biomolecules which are arranged at a greater distance from the surface of the network in its interior.

Thus, there is a need for improved polymer networks.

3. SUMMARY

This disclosure provides three-dimensional polymer networks comprising a crosslinked polymer and one or more channels that extend from a surface and/or near a surface of the network into the network's interior. The networks are suitably covalently attached to a surface. One or more probes, such as a biomolecule, can be immobilized on the surface of the network and throughout the interior of the network, providing a sensor for detecting the presence of and/or measuring the amount of an analyte in a sample. For example, nucleic acid probes can be used to detect complementary nucleic acids present in a sample and antibody probes can be used to detect antigens present in a sample. The networks of the disclosure allow for faster hybridization of a given amount of analyte than networks lacking channels because the channels can effectively increase the surface area of the network, exposing more probes to the sample in a given amount of time. Additionally, the networks of the disclosure can bind more analyte than the same volume of a channel-free network because the channels decrease or eliminate the problem whereby analyte or other components of a sample bound to probes at or near the surface of the network block access to probes located in the interior of the network. Another advantage of the networks of the disclosure is that the high amount of analyte loading made possible by the channels allows for a more sensitive detection of analyte than may be possible with a channel-free network, i.e., the signal to noise ratio can be improved compared to channel-free networks because a given amount of analyte can be concentrated in a smaller network volume. Yet another advantage of the networks of the disclosure is that the high analyte loading made possible by the channels allows for quantification of a wider range of analyte concentrations compared to channel-free networks.

This disclosure also provides arrays comprising a plurality of the three-dimensional networks of the disclosure and a substrate. Arrays of the disclosure can be used to detect and/or measure one or more analytes in one or more samples simultaneously. The arrays of the disclosure can be washed and reused, providing a significant cost advantage over single use arrays. Another advantage of the arrays of the disclosure is that they can be manufactured in a simple manner because all of the components needed to make an individual network can be applied as a single mixture onto a surface of the substrate during the manufacturing process.

This disclosure also provides processes for making the three-dimensional networks and arrays of the disclosure. The three-dimensional networks of the disclosure can be made by crosslinking a polymer in the presence of salt crystals, preferably needle-shaped salt crystals, and subsequently dissolving the salt crystals to leave behind channels in the crosslinked polymer network.

This disclosure also provides processes for using the three-dimensional networks and arrays of the disclosure to detect and/or measure an analyte in a sample, preferably a liquid sample.

4. BRIEF DESCRIPTION OF THE FIGURES

FIG. 14 shows a table showing the mean of the measured values and standard error of the mean, for different spots in Example 2.

5. DETAILED DESCRIPTION

5.1. Three-Dimensional Polymer Networks

Figure 1:
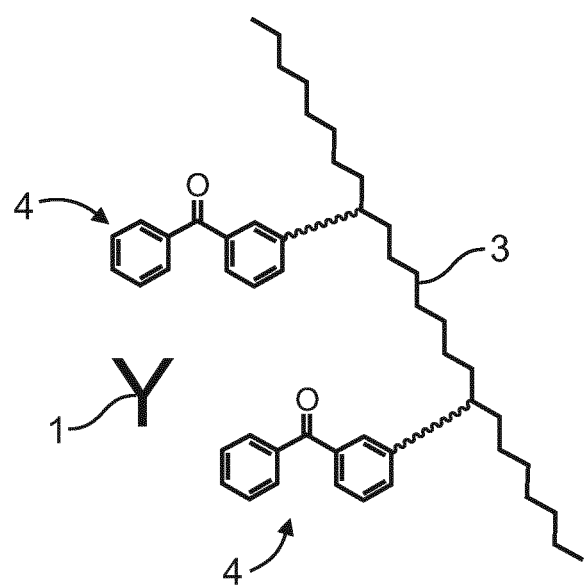
FIG. 1 shows a diagrammatic representation of a mixture which has a probe biomolecule (1) and a polymer (3) comprising two photoreactive groups (4) per molecule dissolved in an aqueous salt solution.

The three-dimensional networks of the disclosure comprise a crosslinked polymer, e.g., a polymer according to Rendl et al., 2011, Langmuir 27:6116-6123 or US 2008/0293592, the contents of which are incorporated by reference in their entireties herein. The three-dimensional networks of the disclosure further comprise one or more channels and can optionally further comprise one or more probes immobilized on the network.

Polymers that can be used to make the networks are described in Section 5.1.1. Cross-linkers than can be used to make the networks are described in Section 5.1.2. Features of the one or more channels are described in Section 5.1.3. Probes that can be immobilized on the networks are described in Section 5.1.4.

5.1.1. Polymers

The three-dimensional networks of the disclosure can comprise a crosslinked homopolymer, copolymer, mixtures of homopolymers, mixtures of copolymers, or mixtures of one or more homopolymers and one or more copolymers. The term "polymer" as used herein includes both homopolymers and/or copolymers. The term "copolymer" as used herein includes polymers polymerized from two or more types of monomers (e.g., bipolymers, terpolymers, quaterpolymers, etc.). Copolymers include alternating copolymers, periodic copolymers, statistical copolymers, random copolymers, block copolymers, linear copolymers and branched copolymers. The three-dimensional networks of the disclosure can comprise any combination of the foregoing types of polymers. Reagents and methods for making such polymers are known in the art (see, e.g., Ravve, A., *Principles of Polymer Chemistry*, Springer Science+Business Media, 1995; Cowie, J. M. G., *Polymers: Chemistry & Physics of Modern Materials*, 2$^{nd}$ Edition, Chapman & Hall, 1991; Chanda, M., *Introduction to Polymer Science and Chemistry: A Problem-Solving Approach*, 2$^{nd}$ Edition, CRC Press, 2013; Nicholson, J. W., *The Chemistry of Polymers*, 4$^{th}$ Edition, RSC Publishing, 2012; the contents of each of which are herein incorporated by reference in their entirety).

Preferred polymers are hydrophilic and/or contain hydrophilic groups. The polymer can be water soluble. In an embodiment, the polymer is a copolymer that has been polymerized from two or more species of monomers selected to provide a desired level of water solubility. For example, water solubility of a copolymer can be controlled by varying the amount of a charged monomer, e.g., sodium 4-vinylsulfonate, used to make the copolymer.

When crosslinked, water soluble polymers form water-swellable gels or hydrogels. Hydrogels absorb aqueous solutions through hydrogen bonding with water molecules. The total absorbency and swelling capacity of a hydrogel can be controlled by the type and degree of cross-linkers used to make the gel. Low crosslink density polymers generally have a higher absorbent capacity and swell to a larger degree than high crosslink density polymers, but the gel strength of high crosslink density polymers is firmer and can maintain network shape even under modest pressure.

A hydrogel's ability to absorb water is a factor of the ionic concentration of the aqueous solution. In certain embodiments, a hydrogel of the disclosure can absorb up to 50 times its weight (from 5 to 50 times its own volume) in deionized, distilled water and up to 30 times its weight (from 4 to 30 times its own volume) in saline. The reduced absorbency in saline is due to the presence of valence cations, which impede the polymer's ability to bond with the water molecule.

The three-dimensional network of the disclosure can comprise a copolymer that has been polymerized from one, two, three, or more than three species of monomers, wherein one, two, three or more than three of the species of monomers have a polymerizable group independently selected from an acrylate group (e.g., acrylate, methacrylate, methyl methacrylate, hydroxyethyl methacrylate, ethyl acrylate, 2-phenyl acrylate), an acrylamide group (e.g., acrylamide, methacrylamide, dimethylacrylamide, ethylacrylamide), an itaconate group (e.g., itaconate, 4-methyl itaconate, dimethyl itaconate) and a styrene group (e.g. styrene, 4-methyl styrene, 4-ethoxystyrene). Preferred polymerizable groups are acrylate, methacrylate, ethacrylate, 2-phenyl acrylate, acrylamide, methacrylamide, itaconate, and styrene. In some embodiments, one of the monomers used to make the copolymer is charged, e.g., sodium 4-vinylbenzenesulfonate.

Figure 10:
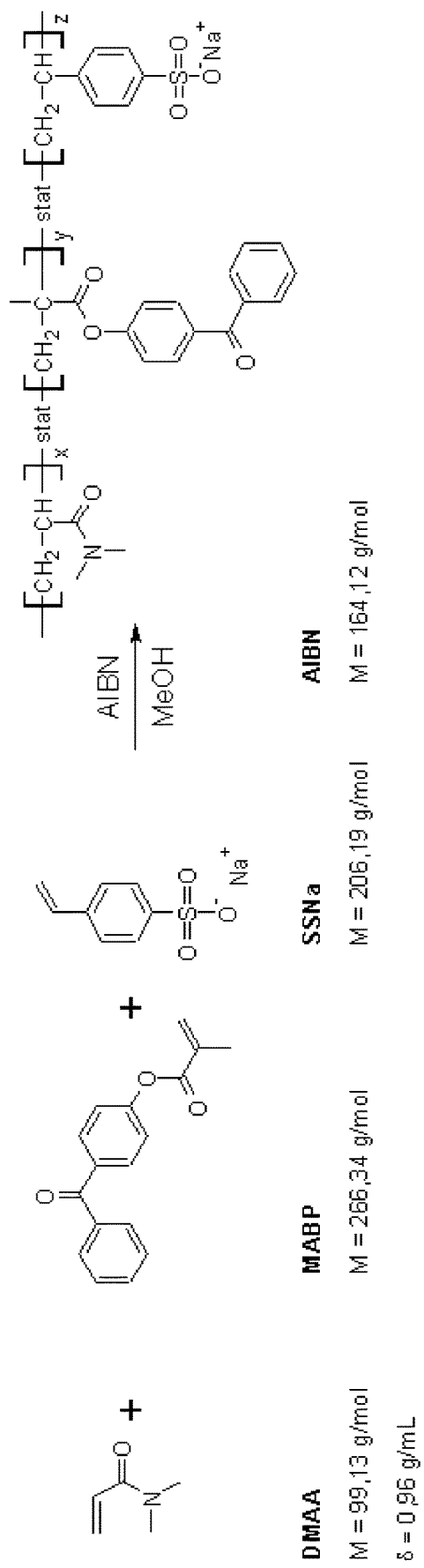
FIG. 10 shows a reaction pathway for the formation of p(Dimethylacrylamide co methacryloyloxybenzophenone co Sodium 4-vinylbenzenesulfonate).

The polymer used to make a network of the disclosure can comprise at least one, at least two, or more than two cross-linker groups per molecule. A cross-linker group is a group that covalently bonds the polymer molecules of the network to each other and, optionally, to probes and/or a substrate. Copolymers that have been polymerized from two or more monomers (e.g., monomers having a polymerizable group independently selected from those described in the preceding paragraph), at least one of which comprises a cross-linker, are suitable for making a three-dimensional network of the disclosure. Exemplary cross-linkers are described in Section 5.1.2. A preferred monomer comprising a cross-linker is methacryloyloxybenzophenone (MABP) (see FIG. 10).

In a preferred embodiment, the copolymer is a bipolymer or a terpolymer comprising a cross-linker. In a particularly preferred embodiment, the copolymer comprises p(Dimethylacrylamide co methacryloyloxybenzophenone co Sodium 4-vinylbenzenesulfonate) (see FIG. 10).

5.1.2. Cross-Linkers

Crosslinking reagents (or cross-linkers) suitable for making the crosslinks in the three-dimensional networks include those activated by ultraviolet light (e.g., long wave UV light), visible light, and heat. Exemplary cross-linkers activated by UV light include benzophenone, thioxanthones (e.g., thioxanthen-9-one, 10-methylphenothiazine) and benzoin ethers (e.g., benzoin methyl ether, benzoin ethyl ether). Exemplary cross-linkers activated by visible light include ethyl eosin, eosin Y, rose bengal, camphorquinone and erythirosin. Exemplary cross-linkers activated by heat include 4,4' azobis(4-cyanopentanoic) acid, and 2,2-azobis [2-(2-imidazolin-2-yl) propane] dihydrochloride, and benzoyl peroxide. Other cross-linkers known in the art, e.g., those which are capable of forming radicals or other reactive groups upon being irradiated, may also be used.

5.1.3. Channels

The three-dimensional networks of the disclosure contain one or more channels.

As used herein, a "channel" is an elongated passage in a network that (1) is substantially straight, and (2) in the hydrated state of the network, has a minimum cross-section that is at least 500 nm and a length that is at least five times, and preferably at least ten times, the minimum cross-section of the passage. For example, the length of the channel can be 5 to 15 times, 5 to 10 times, or 10 to 15 times the minimum cross-section of the channel. A channel that is "substantially straight" is one which extends from a point of nucleation in one direction without changing direction more than 45 degrees in any direction, i.e., the X, Y or Z direction.

The "hydrated state of the network" means that the network is at equilibrium with respect to water absorption, i.e., it absorbs in aqueous solution as much water as it emits.

Channels can allow access to the interior of the network. Although channels can have a relatively large channel cross-section, the network can remain mechanically stable because the mesh size of the network can be significantly smaller than the channel cross-section. The channels can form a sort of highway, through which analytes can enter quickly into the interior of the network. The transport of the analytes can be effected in the channel by diffusion and/or convection.

The channels can extend from a surface or near the surface of the network into the interior of the network. For example, the one or more channels can extend from a point that is less than 10 microns, less than 9 microns, less than 8 microns, less than 7 microns, less than 6 microns, less than 5 microns, less than 4 microns, less than 3 microns, less than 2 microns, less than 1 micron from the surface of the network, or extends into the interior from a point on the surface of the network. The network can contain a plurality of channels (e.g., 2 to 100, 2 to 50, 2 to 25, 2 to 10, 10 to 50, 10 to 25, or 25 to 50), each of which can extend from a surface or near a surface of the network into the interior of the network. In preferred embodiments, the network contains 10, 20, 30, 40 or 50 channels, or a number of channels ranging between any two of the foregoing values (e.g., 10 to 50, 20 to 40, 30 to 50, 10 to 20, 20 to 30, 30 to 40, or 40 to 50 channels). In a specific preferred embodiment, the network contains 10 to 50 channels.

In some embodiments, the length of at least one channel is 10 to 100%, 10% to 90%, 10% to 80%, 10% to 70%, 10% to 60%, 10% to 50%, 10% to 40%, 10% to 30%, 10% to 15%, 10% to 20%, 10% to 25%, 10 to 30%, 15% to 20%, 15% to 25%, 15% to 30%, 20 to 25%, or 25% to 30% of the largest dimension of the network. In preferred embodiments, the length of at least one channel is approximately 10%, 20%, 30%, 40% or 50% of the largest dimension of the network, and in some embodiments has a length ranging between any pair of the foregoing embodiments (e.g., 10% to 50%, 10% to 30%, 30% to 50%, 10% to 20%, 20% to 30%, 30% to 40%, or 40% to 50% of the largest dimension of the network). In a specific preferred embodiment, the length is 10% to 50% of the largest dimension of the network.

In some embodiments, the network comprises at least one channel having a minimum cross-section of at least 5 times, at least 10 times, at least 15 times, or at least 20 times the mesh size (e.g., 5 to 10 times, 5 to 15 times, 5 to 20 times, 5 to 25 times, 5 to 30 times, 10 to 15 times, 10 to 20 times, 10 to 25 times, 10 to 30 times, 10 to 15 times, 10 to 20 times, 10 to 25 times, 10 to 30 times, 15 to 20 times, 15 to 25 times, 15 to 30 times, 20 to 25 times, 20 to 30 times, or 25 to 30 times the network's mesh size). In preferred embodiments, the network comprises at least one channel having a minimum cross-section of 10 to 30 times the mesh size. This ensures a high stability of the polymer network, and can also prevent network penetration and binding by undesirable larger molecules or components in a sample.

The network can have a mesh size (measured in the hydrated state of the network) of, for example, 5 to 75 nm (e.g., 10 to 20 nm, 10 to 30 nm, 10 to 40 nm, 10 to 50 nm, 20 to 30 nm, 20 to 40 nm, 20 to 50 nm, 30 to 40 nm, 30 to 50 nm, or 40 to 50 nm).

The networks of the disclosure can comprise a plurality of channels (e.g., 2 to 100, 2 to 50, 2 to 25, 2 to 10, 10 to 50, 10 to 25, or 25 to 50), and each channel can independently have one or more of the features described in this section. In some embodiments, the majority of the channels have one or more features described in this section. In a specific preferred embodiment, the network contains 10 to 50 channels that each have one or more of the features described in this section.

Preferred three-dimensional networks contain a plurality of channels that converge at a point located within the network, and are arranged such that, starting from the surface of the network towards the interior, the lateral distance between the channels decreases. In some embodiments, a plurality of channels extend approximately radially away from a point situated in the interior of the network. In some embodiments, the three-dimensional network contains multiple pluralities of channels (e.g., 2, 3, 4, 5, 6, 7, 8, 9, or 10 pluralities of channels), each plurality converging at a different point within the network. In certain aspects, a plurality (or each plurality) are connected at the point of their convergence.

The presence of a channel in a network can be verified using the following procedure:

The network is brought into contact with an aqueous liquid at room temperature, for example, in a bowl. The liquid contains a plurality of nanoparticles which are larger than the mesh size of the network and smaller than the minimum cross-section of the channel. Thus, nanoparticles can enter the channel and spread along the channel. Without being bound by theory, it is believed that this can occur due to the Brownian molecular motion and/or convection through the liquid in the channel. Such nanoparticles are known as quantum dots. They can, for example, have a diameter of about 10 nanometers.

An incubation period is selected so that the network in the liquid is completely hydrated, i.e., that the network on average takes the same amount of water as it releases.

The incubation period can be, for example, one hour. The penetration of the nanoparticles in the channel can be accelerated by setting in motion the network and/or the liquid during the incubation, for example, by vibrating the network and/or liquid, preferably by means of ultrasonic waves.

After completion of the incubation, the liquid is separated from the network, for example, by draining the liquid from the bowl or taking the network out of the bowl.

Then, the hydrated network is frozen, for example, by means of liquid nitrogen. Thereafter, the frozen network can be cut with the aid of a cryomicrotome along mutually parallel cutting planes into thin slices. The cutting planes are arranged transversely to the longitudinal extension of the channel and penetrate the channel. The cutting is preferably carried out using a liquid nitrogen-cooled diamond blade. The thickness of the slices can be, for example, about 100 nm or 200 nm.

With the aid of a microscope, the nanoparticles disposed in the disks obtained by cutting the frozen network are located. The nanoparticles can be fluorescent and optically highlighted so that they can be better distinguished from the network, if necessary. The locating of the nanoparticles can be done using a suitable software with image processing methods. To examine the disks, preferably a confocal microscope laser scanning microscope with fluorescence optics or an electron microscope is used.

The geometry and/or position information of the nanoparticles obtained in this manner may be, with the aid of a computer, used to make a three-dimensional geometric model of distribution of the nanoparticles in the network. The model can then be used to determine whether the arrangement of the nanoparticles in the network comprises at least one substantially straight region whose cross-section is in no place smaller than 500 nm and whose length corresponds at least to the five-fold of its smallest cross-section. If this condition is fulfilled it is determined that the network comprises at least one channel.

Alternatively, the three-dimensional distribution of the nanoparticles can be determined in the network by means of micro-3D X-ray computer tomography.

5.1.4. Probes

A probe immobilized on the network of the disclosure can be a biomolecule or a molecule that binds a biomolecule, e.g., a partner of a specifically interacting system of complementary binding partners (receptor/ligand). For example, probes can comprise nucleic acids and their derivatives (such as RNA, DNA, locked nucleic acids (LNA), and peptide nucleic acids (PNA)), proteins, peptides, polypeptides and their derivatives (such as glucosamine, antibodies, antibody fragments, and enzymes), lipids (e.g., phospholipids, fatty acids such as arachidonic acid, monoglycerides, diglycerides, and triglycerides), carbohydrates, enzyme inhibitors, enzyme substrates, antigens, and epitopes. Probes can also comprise larger and composite structures such as liposomes, membranes and membrane fragments, cells, cell lysates, cell fragments, spores, and microorganisms.

A specifically interacting system of complementary bonding partners can be based on, for example, the interaction of a nucleic acid with a complementary nucleic acid, the interaction of a PNA with a nucleic acid, or the enzyme/substrate, receptor/ligand, lectin/sugar, antibody/antigen, avidin/biotin or streptavidin/biotin interaction.

Nucleic acid probes can be a DNA or an RNA, for example, an oligonucleotide or an aptamer, an LNA, PNA, or a DNA comprising a methacyrl group at the 5' end (5' Acrydite™). Oligonucleotide probes can be, for example, 12 to 30, 14 to 30, 14 to 25, 14 to 20, 15 to 30, 15 to 25, 15 to 20, 16 to 30, 16 to 25, 16 to 20, 15 to 40, 15 to 45, 15 to 50, 15 to 60, 20 to 55, 18 to 60, 20 to 50, 30 to 90, 20 to 100, 20 to 60, 40 to 80, 40 to 100, 20 to 120, 20 to 40, 40 to 60, 60 to 80, 80 to 100, 100 to 120 or 12 to 150 nucleotides long. In preferred embodiments, the oligonucleotide probe is 15 to 60 nucleotides in length.

When using a nucleic acid probe, all or only a portion of the probe can be complementary to the target sequence. The portion of the probe complementary to the target sequence is preferably at least 12 nucleotides in length, and more preferably at least 15, at least 18 or at least 20 nucleotides in length. For nucleic acid probes of greater length than 40 or 50 nucleotides, the portion of the probe complementary to the target sequence can be at least 25, at least 30 or at least 35 nucleotides in length.

The antibody can be, for example, a polyclonal, monoclonal, or chimeric antibody or an antigen binding fragment thereof (i.e., "antigen-binding portion") or single chain thereof, fusion proteins comprising an antibody, and any other modified configuration of the immunoglobulin molecule that comprises an antigen recognition site, including, for example without limitation, single chain (scFv) and domain antibodies (e.g., human, camelid, or shark domain antibodies), maxibodies, minibodies, intrabodies, diabodies, triabodies, tetrabodies, vNAR and bis-scFv (see e.g., Hollinger and Hudson, 2005, Nature Biotech 23:1126-1136). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. "Antibody" also encompasses any of each of the foregoing antibody/immunoglobulin types.

Three-dimensional networks of the disclosure can comprise a single species of probe or more than one species of probe (e.g., 2, 3, 4, or 5 or more species). Three-dimensional networks can comprise more than one species of probe for the same target (e.g., antibodies binding different epitopes of the same target) and/or comprise probes that bind multiple targets.

The networks can comprise a labeled (e.g., fluorescently labeled) control probe molecule that can be used, for example, to measure the amount probe present in the network.

The probes can be distributed throughout the network (e.g., on a surface and the interior of a network). Preferably, at least one probe is spaced away from the surface of the network and adjoins at least one channel. A probe so located is then directly accessible for analyte molecules or analyte components through the channel. In some embodiments, a majority of the probes are located in the interior of the network.

The one or more probes can be immobilized on the network covalently or non-covalently. For example, a probe can be crosslinked to the crosslinked polymer or a probe can be non-covalently bound to the network (such as by binding to a molecule covalently bound to the network). In a preferred embodiment, one or more probes are crosslinked to the crosslinked polymer. In some embodiments, a majority of the probes are covalently bound in the interior of the network (e.g., such that at least a portion of the probes adjoin a channel).

Without being bound by theory, the inventors believe that the processes described in Section 5.3 for manufacturing three-dimensional networks in the presence of salt crystals (particularly phosphate salt crystals) may result in a greater concentration of probe molecule at or near the interface between the polymer and the channel due to electrostatic interactions between the probe molecules (particularly nucleic acid probe molecules) and the salt crystals. Accordingly, in some embodiments of the invention, the disclosure provides networks according to the disclosure in which the probe density is greater at the interface between the polymer and the channels than within regions of the polymer not abutting a channel. In various embodiments, the probe density is at least 10%, at least 20%, at least 30%, at least 40%, or at least 50% more dense at the interface between the polymer and the channels than within regions of the polymer not abutting a channel.

The density of probe molecule in a network can be verified using the following procedure:

The network is brought into contact with an aqueous liquid at room temperature, for example, in a bowl. The liquid contains a plurality of nanoparticles attached to a moiety that interacts with the probe molecules in the network, for example streptavidin if the probe molecules are biotinylated. The size of the nanoparticles is smaller than the mesh size of the network and smaller than the minimum cross-section of the channel to allow the nanoparticles to become distributed throughout the polymer. Suitable nanoparticles are quantum dots 2-5 nanometers in dimeter.

An incubation period is selected so that the network in the liquid is completely hydrated, i.e., that the network on average takes the same amount of water as it releases. The incubation period can be, for example, one hour. The penetration of the nanoparticles in the network can be accelerated by setting in motion the network and/or the liquid during the incubation, for example, by vibrating the network and/or liquid, preferably by means of ultrasonic waves.

After completion of the incubation, the liquid is separated from the network, for example, by draining the liquid from the bowl or taking the network out of the bowl.

Then, the hydrated network is frozen, for example, by means of liquid nitrogen. Thereafter, the frozen network can be cut with the aid of a cryomicrotome along mutually parallel cutting planes into thin slices. The cutting planes are arranged transversely to the longitudinal extension of the channel and penetrate the channel. The cutting is preferably carried out using a liquid nitrogen-cooled diamond blade. The thickness of the slices can be, for example, about 100 nm or 200 nm.

With the aid of a microscope, the nanoparticles disposed in the disks obtained by cutting the frozen network are located. The nanoparticles can be fluorescent and optically highlighted so that they can be better distinguished from the network, if necessary. The locating of the nanoparticles can be done using a suitable software with image processing methods. To examine the disks, preferably a confocal microscope laser scanning microscope with fluorescence optics or an electron microscope is used.

The geometry and/or position information of the nanoparticles obtained in this manner may be, with the aid of a computer, used to make a three-dimensional geometric model of distribution of the nanoparticles in the network. The model can then be used to determine whether the distribution of nanoparticles reflects a greater density of probe molecules near sites of channels.

5.2. Arrays

The three-dimensional networks of the disclosure can be positioned (e.g., deposited) on a substrate, and are preferably immobilized on a substrate (e.g., by covalent crosslinks between the network and the substrate). A plurality of networks can be immobilized on a substrate to form an array useful, for example, as a biochip.

Suitable substrates include organic polymers, e.g., cycloolefin copolymers (COCs), polystyrene, polyethylene, polypropylene and polymethylmethacrylate (PMMA, Plexiglas®). Ticona markets an example of a suitable COC under the trade name Topas®. Inorganic materials (e.g., metal, glass) can also be used as a substrate. Such substrates can be coated with organic molecules to allow for crosslinks between the network and a surface of the substrate. For example, inorganic surfaces can be coated with self-assembled monolayers (SAMs). SAMs can themselves be completely unreactive and thus comprise or consist of, for example, pure alkyl silanes. Other substrates can also be suitable for crosslinking to the three-dimensional network provided they are able to enter into stable bonds with organic molecules during free-radical processes (e.g., organoboron compounds).

The substrate can be rigid or flexible. In some embodiments, the substrate is in the shape of a plate (e.g., a rectangular plate, a square plate, a circular disk, etc.). For example, the substrate can comprise a microwell plate, and the three-dimensional networks can be positioned in the wells of the plate.

Figure 11:
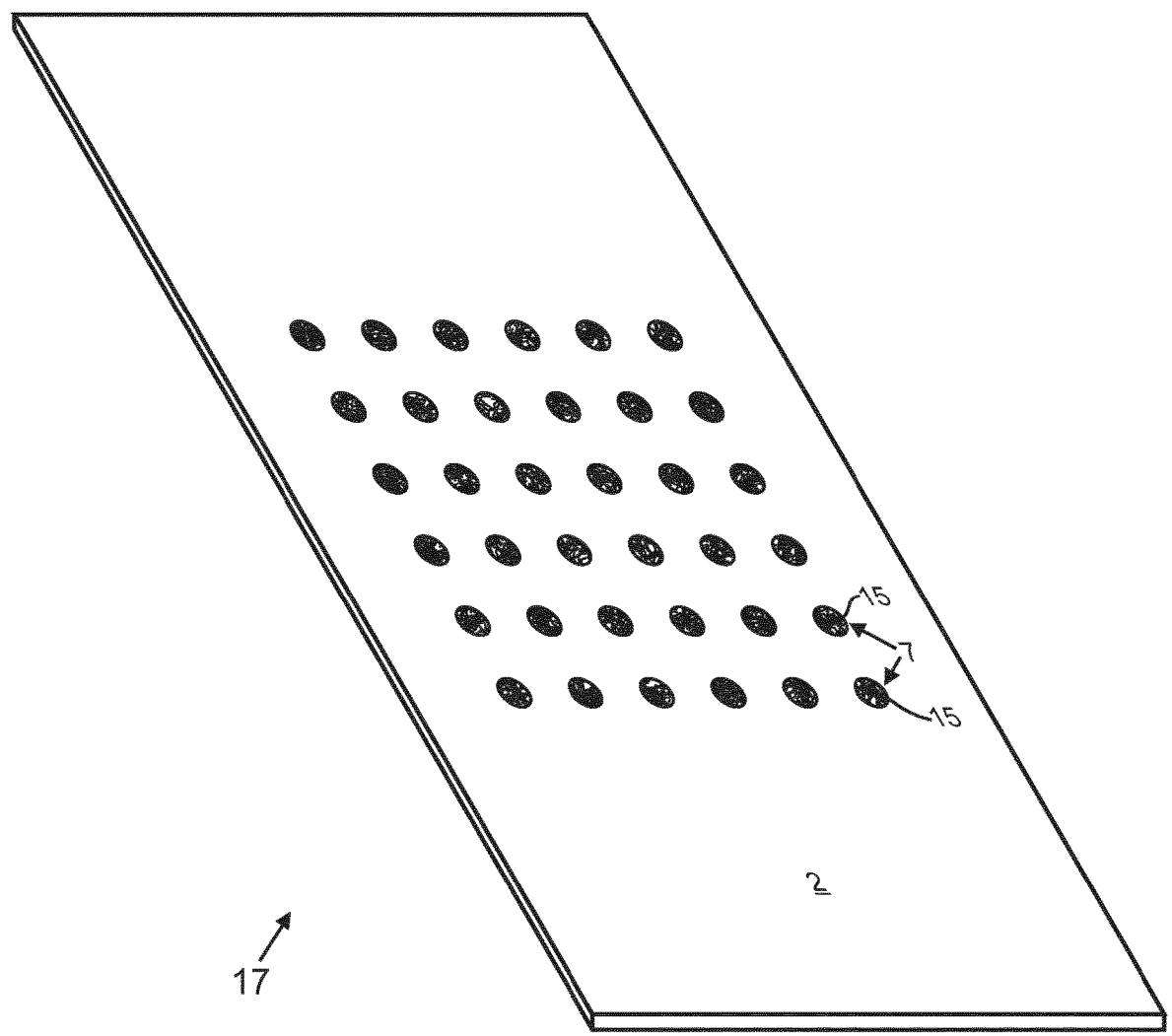
FIG. 11 shows a perspective view of a biochip (17) having an organic surface (2) on which polymer networks (15) are located at spots (7) arranged as a matrix of rows and columns.
Figure 12:
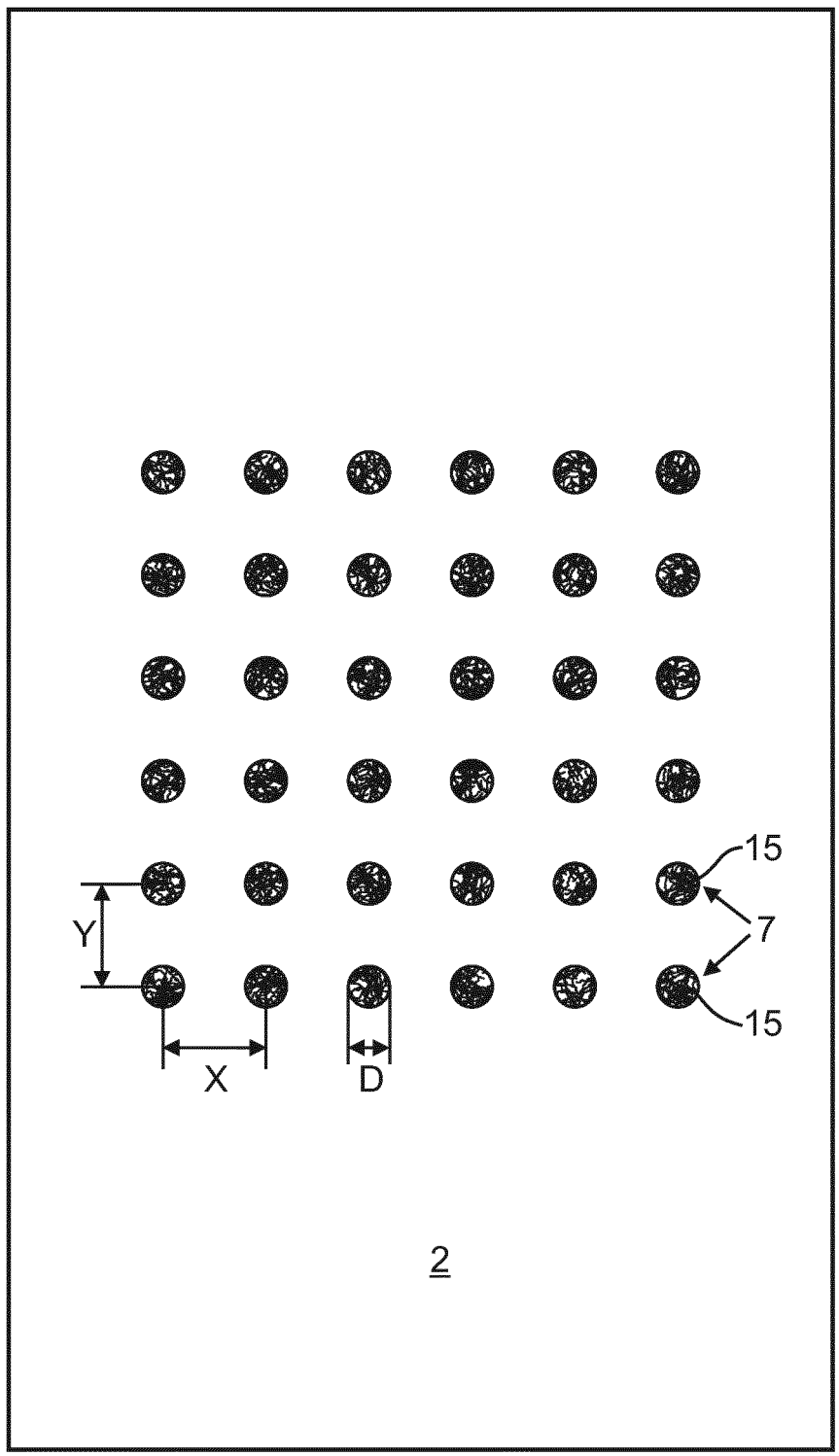
FIG. 12 shows a top view of a biochip (17) as shown in FIG. 11, where each polymer network (15) has a diameter (D), and where the rows and columns are separated by a distance Y and a distance X, respectively, measured from the center points of the polymer networks (15).

The individual networks can be positioned at distinct spots on a surface of the substrate, e.g., in a matrix comprising a plurality of columns and rows. In the embodiment shown in FIG. 11, the networks are located at 36 spots arranged in six columns and six rows. Arrays having different numbers of rows and columns, the number of each of which can be independently selected, are contemplated (e.g., 2 to 64 columns and 2 to 64 rows). The columns can be separated by a distance X and the rows can be separated by a distance Y (for example, as shown in FIG. 12) so as to form a grid of spots on which the individual networks can be located. X and Y can be selected so that the networks, located at the spots of the grid, do not contact each other in the dehydrated state and do not contact each other in the hydrated state. The dimensions X and Y can be the same or different. In some embodiments, X and Y are the same. In some embodiments, X and Y are different. In some embodiments, X and Y are independently selected from distances of at least about 500 µm (e.g., 500 µm to 5 mm, 500 µm to 4 mm, 500 µm to 3 mm, 500 µm to 2 mm, or 500 µm to 1 mm). In some embodiments, X and Y are both about 500 µm. In other embodiments, X and Y are both 500 µm.

Figure 13:
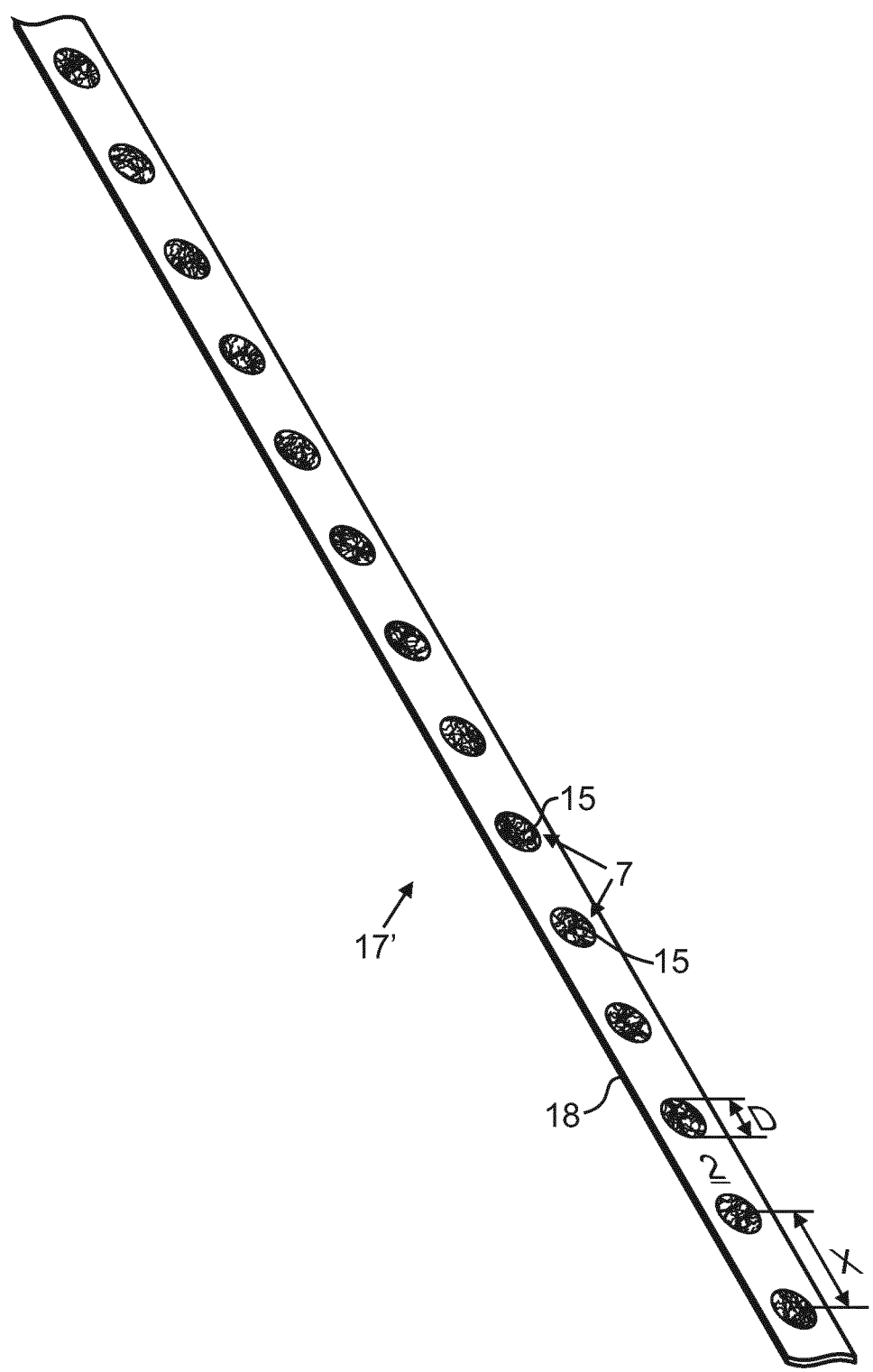
FIG. 13 shows a biosensor (17') comprising a flexible substrate band (18) having an organic surface (2) on which polymer networks (15) having a diameter (D) are located at spots (7) separated by distance X measured from the center points of the polymer networks.
Figure 15:
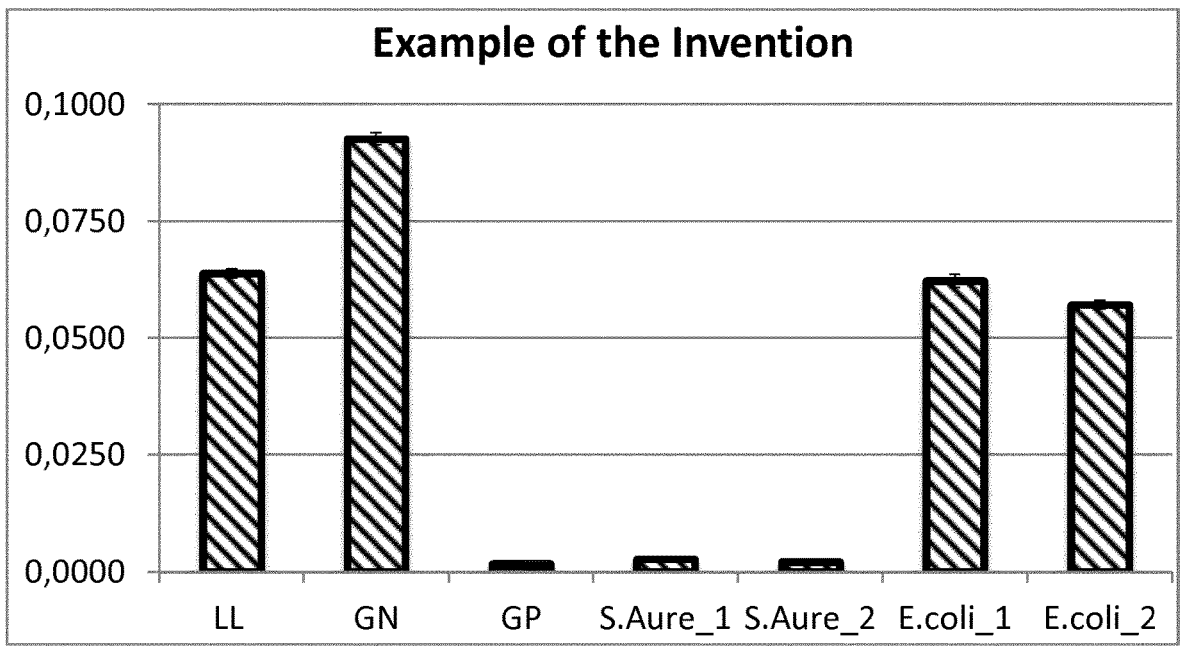
FIG. 15 is a graphic representation of the mean of the measured values obtained by the array of Section 7.2.1.
Figure 16:
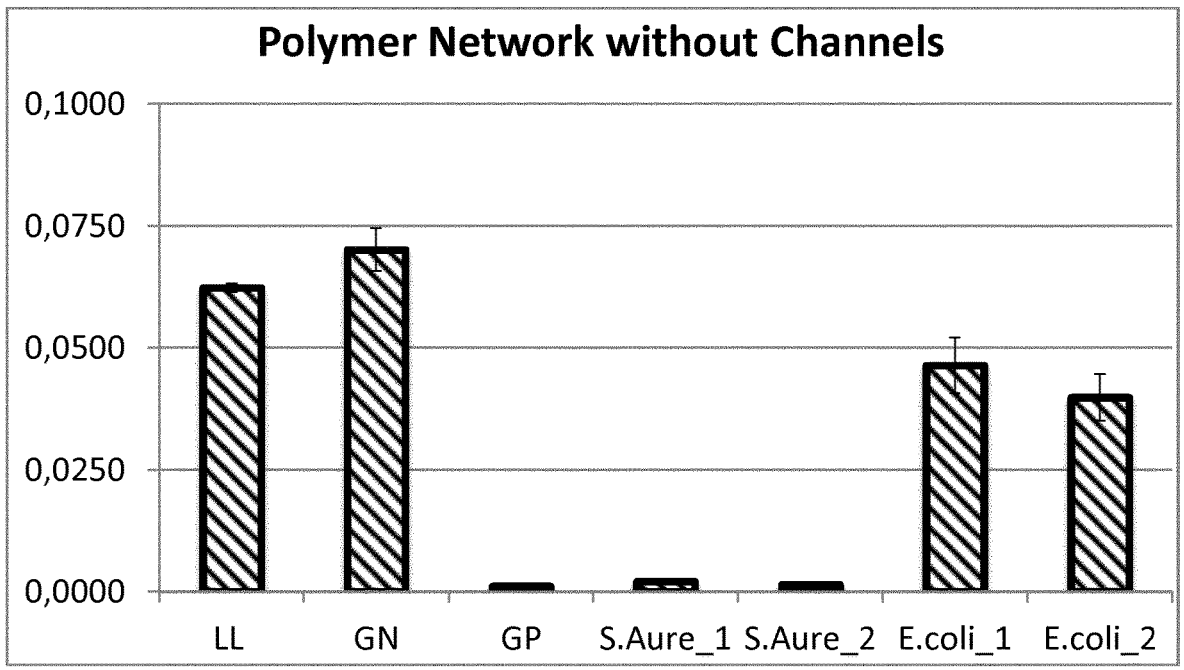
FIG. 16 is a graphic representation of the mean of the measured values obtained by an array of Section 7.2.2.

In some embodiments, substrate is band-shaped (for example, as shown in FIG. 13). The networks can be arranged as a single row extending in the longitudinal direction of a band-shaped organic surface, or can be arranged as multiple rows extending in the longitudinal direction of the band-shaped surface. The rows and columns in such band-shaped arrays can have grid dimensions X and Y as described above.

The individual networks can each cover an area of the surface of the array that is circular or substantially circular. Typically, the diameter of the area on the surface of the array covered by the individual networks (i.e., the spot diameter) is 80 µm to 1000 µm. In various embodiments, the spot diameter is 80 µm, 100 µm, 120 µm, 140 µm, 160 µm, 180

µm, 200 µm, 300 µm, 400 µm, 500 µm, 600 µm, 700 µm, 800 µm, 900 µm, or 1000 µm, or selected from a range bounded by any two of the foregoing embodiments, e.g., 80 µm to 200 µm, 100 µm to 120 µm, 120 µm to 140 µm, 120 µm to 180 µm, 140 µm to 160 µm, 160 µm to 180 µm, 180 µm to 200 µm, 120 µm to 200 µm, 100 µm to 400 µm, 160 µm to 600 µm, or 120 µm to 700 µm, and so on and so forth. In a preferred embodiment, the diameter ranges from 100 µm to 200 µm or a subrange thereof.

The arrays of the disclosure typically have at least 8 individual three-dimensional networks. In certain aspects, the arrays have at least 16, at least 24, at least 48, at least 96, at least 128, at least 256, at least 512, or at least 1024 individual three-dimensional networks. In some embodiments, the arrays of the disclosure have 24, 48, 96, 128, 256, 512, 1024, 2048, 4096 or 8192 individual networks, or have a number of three-dimensional networks selected from a range bounded any two of the foregoing embodiments, e.g., from 8 to 128, 8 to 512, 24 to 8192, 24 to 4096, 48 to 2048, 96 to 512, 128 to 1024, 24 to 1024, 48 to 512, 96 to 1024, or 128 to 512 three-dimensional networks, and so on and so forth. In a preferred embodiment, number of three-dimensional networks on an array ranges from 8 to 1024. In a particularly preferred embodiment, the number of three-dimensional networks on an array ranges from 25 to 400.

The individual networks which comprise the arrays of the disclosure can have identical or different probes (e.g., each network can have a unique set of probes, multiple networks can have the same set of probes and other networks can have a different set or sets of probes, or all of networks can have the same set of probes). For example, networks arranged in the same row of a matrix can comprise the same probes and the networks arranged in different rows of the matrix can have different probes.

Typically, the individual networks on an array vary by no more than 20%, no more than 15%, no more than 10% or no more than 5% from one another by spot diameter and/or network volume.

In some embodiments, the arrays comprise one or more individual networks (e.g., spots on an array) with one or more control oligonucleotides or probe molecules. The control oligonucleotides can be labelled, e.g., fluorescently labelled, for use as a spatial control (for spatially orienting the array) and/or a quantifying the amount of probe molecules bound to the networks, for example, when washing and reusing an array of the disclosure (i.e., as a "reusability control"). The spatial and reusability control probes (which can be the same or different probes) are referred to in Section 7.2 as a "landing light", where the same probe is used for both purposes.

The same spot on the array or a different spot on the array can further include an unlabelled probe that is complementary to a known target. When used in a hybridization assay, determining the signal strength of hybridization of the unlabelled probe to the labelled target can determine the efficiency of the hybridization reaction. When an individual network (i.e., a spot on an array) is used both as a reusability and/or spatial control and a hybridization control, a different fluorescent moiety can be used to label the target molecule than the fluorescent moiety of the reusability control or spatial control probes.

In some embodiments, the arrays of the disclosure can be reused at least 5 times, at least 10 times, at least 20 times, at least 30 times, at least 40 times, or at least 50 times (e.g., 5 to 20 times, 5 to 30 times, 10 to 50 times, 10 to 20 times, 10 to 30 times, 20 to 40 times, or 40 to 50 times, preferably comprising reusing the array 10 to 50 times). The array can be washed with a salt solution under denaturing conditions (e.g., low salt concentration and high temperature). For example, the array can be washed with a 1-10 mM phosphate buffer at 80-90° C. between uses. The temperature of the wash can be selected based upon the length (Tm) of the target:probe hybrid.

The integrity of an array can be determined by a "reusability control" probe. The reusability control probe can be fluorescently labeled or can be detected by hybridization to a fluorescently labeled complementary nucleic acid. The fluorescent label of a fluorescently labeled reusability control probe may be bleached by repeated excitation, before the integrity of the nucleic acid is compromised; in such cases any further reuses can include detection of hybridization to a fluorescently labeled complementary nucleic acid as a control. Typically, an array of the invention is stable for at least 6 months.

In various embodiments, a fluorescently labeled reusability control probe retains at least 99%, 95% 90%, 80%, 70%, 60%, or 50% of its initial fluorescence signal strength after 5, 10, 20, 30, 40, or 50 uses. Preferably, the reusability control probe retains least 75% of its fluorescence signal strength after 5 or 10 uses. An array can continue to be reused until the reusability control probe retains at least 50% of its fluorescence signal strength, for example after 20, 30, 40 or 50 reuses. The fluorescent signal strength of the control probe can be tested between every reuse, every other reuse, every third reuse, every fourth reuse, every fifth reuse, every sixth reuse, every seventh reuse, every eighth reuse, every ninth reuse, every tenth reuse, or a combination of the above. For example, the signal strength can be tested periodically between 5 or 10 reuses initially and the frequency of testing increased with the number of reuses such that it is tested after each reuse after a certain number (e.g., 5, 10, 20, 30, 40 or 50) uses. In some embodiments, the frequency of testing averages once per 1, 1.5, 2, 2.5, 3, 4, 5 or 10 uses, or averages within a range bounded between any two of the foregoing values, e.g., once per 1-2 uses, once per 1-1.5 uses, once per 1-3 uses, or once per 1.5-3 uses.

It is noted that the nomenclature of "spatial control", "reusability control" and "hybridization control" is included for convenience and reference purposes and is not intended to connote a requirement that the probes referred to "spatial control", "reusability control" and "hybridization control" be used as such.

5.3. Processes For Making Three-Dimensional Polymer Networks

In one aspect, the processes of the disclosure for making three-dimensional polymer networks comprise (a) exposing a mixture comprising an aqueous salt solution, a polymer, a cross-linker and, optionally, one or more probes to salt crystal forming conditions, (b) exposing the mixture to crosslinking conditions to crosslink the polymer for form a crosslinked polymer network, and (c) contacting the crosslinked polymer network with a solvent to dissolve the salt crystals and form one or more channels.

The processes can further comprise a step of forming the mixture by combining an aqueous salt solution, a polymer, a cross-linker and, optionally, one or more probes, and/or further comprise a step of applying the mixture to a substrate (e.g., a substrate described in Section 5.2) prior to exposing the mixture to salt forming conditions. If the polymer being used has a pre-attached cross-linker (e.g., when using a copolymer polymerized from a monomer comprising a cross-linker), the step of forming the mixture can comprise combining an aqueous salt solution with the polymer and, optionally, one or more probes.

The channels formed by dissolution of the salt crystals can have one or more of the features described in Section 5.1.3.

The mixture can be applied to a substrate prior to exposing the mixture to salt forming conditions for example, by spraying the mixture onto a surface of the substrate (e.g., at 1024 sites on the surface). The mixture can be applied to the surface using a DNA chip spotter or inkjet printer, for example. In a preferred embodiment, the mixture is sprayed using an inkjet printer. This permits a simple and rapid application of the mixture to a large number of spots on the substrate. The spots can be arranged, for example, in the form of a matrix in several rows and/or columns. Preferably, the salt content in the mixture during printing is below the solubility limit so that the mixture does not crystallize in the printing head of the printer. The volume of mixture applied at individual spots can be, for example, 100 pl, 200 pl, 300 pl, 400 pl, 500 pl, 750 pl, 1 nl, 2 nl, 3 nl, 4 nl, or 5 nl, or can be selected from a range bounded by any two of the foregoing values (e.g., 100 pl to 5 nl, 100 pl to 1 nl, 300 pl to 1 nl, 200 pl to 750 nl, 100 pl to 500 pl, 200 pl to 2 nl, 500 pl to 2 nl 1 nl to 2 nl, and so on and so forth). In preferred embodiments, the spot volume is 200 pl to 4 nl.

The diameter of the individual spots will depend on the composition of the mixture, the volume of the mixture applied, and the surface chemistry of the substrate. Spot diameters typically range between 80 μm to 1000 μm and can be obtained by varying the foregoing parameters. In various embodiments, the spot diameters are 80 μm, 100 μm, 120 μm, 140 μm, 160 μm, 180 μm, 200 μm, 300 μm, 400 μm, 500 μm, 600 μm, 700 μm, 800 μm, 900 μm, or 1000 μm, or selected from a range bounded by any two of the foregoing embodiments, e.g., 80 μm to 200 μm, 100 μm to 120 μm, 120 μm to 140 μm, 120 μm to 180 μm, 140 μm to 160 μm, 160 μm to 180 μm, 180 μm to 200 μm, 120 μm to 200 μm, 100 μm to 400 μm, 160 μm to 600 μm, or 120 μm to 700 μm, and so on and so forth. In a preferred embodiment, the diameter ranges from 100 μm to 200 μm or a subrange thereof.

Suitable polymers, cross-linkers, and probes that can be used in the processes of the disclosure are described in Sections 5.1.1, 5.1.2, and 5.1.4, respectively. In some embodiments, the polymer used in the processes has at least one cross-linker group per polymer molecule. In a preferred embodiment, the polymer has at least two cross-linker groups per molecule. In a particularly preferred embodiment, the polymer has at least two photoreactive cross-linker groups per molecule. In these embodiments, separate polymer and cross-linker molecules are not needed.

Suitable salts that can be included in the mixture are described in Section 5.3.1. Suitable salt forming conditions are described in Section 5.3.2. Suitable crosslinking conditions are described in Section 5.3.3. Suitable solvents for dissolving the salt crystals are described in Section 5.3.4.

5.3.1. Salt

The salt can be selected for its compatibility with one or more probes. Ideally, the salt has one or more of the following characteristics, (i) the salt is not toxic to the probes (e.g., the salt does not denature the probes), (ii) the salt does not react chemically with the probes, (iii) the salt does not attack fluorophores, such as cyanine dyes, which are suitable for the optical marking of probes, (iv) the salt does not react with analytes, detection molecules, and/or binding partners bonded thereto, and/or (v) the salt forms needle-shaped crystals.

In a preferred embodiment, the salt solution comprises monovalent cations. The mixture can comprise disodium hydrogen phosphate and/or sodium dihydrogen phosphate which, in aqueous solution, releases $Na^+$ cations and phosphate ions $PO_4^{3-}$. Sodium phosphate is readily soluble in water and forms colorless crystals.

In a particularly preferred embodiment, the mixture comprises dipotassium hydrogen phosphate ($K_2HPO_4$) and/or potassium dihydrogen phosphate ($KH_2PO_4$). These salts are excellently soluble in water and can therefore form a correspondingly large number of needle-shaped salt crystals in the mixture.

5.3.2. Salt Crystal Forming Conditions

Salt crystal forming conditions can comprise forming in the mixture at least one salt crystal, preferably a needle-shaped salt crystal, by dehydrating the mixture or cooling the mixture until the relative salt content in the mixture increases to above the solubility limit, meaning that the mixture is supersaturated with the salt. This promotes the formation of salt crystals from a crystallization germ located in the volume of the mixture towards the surface of the mixture.

The mixture can be dehydrated by heating the mixture, exposing the mixture to a vacuum, and/or reducing the humidity of the atmosphere surrounding the mixture.

The mixture can be heated by placing the mixture on a heated substrate or surface (e.g., between about 50° ° C. to about 70° C.), heating the substrate or surface on which the mixture has been placed (e.g., to between about 50° C. to about 70° C.), and/or contacting the mixture with a hot gas (e.g., air, nitrogen, or carbon dioxide having a temperature that is higher than the temperature of the mixture) such that water is evaporated from the mixture. The contacting with the hot gas can, for example, take place by placing the mixture in a heating oven. During the transportation to the heating oven, the mixture is preferably kept moist, in particular at a relative humidity of above 75%. As a result of this, an uncontrolled formation of salt crystals during the transportation of the mixture to the heating oven is counteracted. This permits the formation of longer, needle-shaped salt crystals in the heating oven. By heating the mixture it is also possible to activate thermally activatable cross-linkers, if present, and crosslink the polymer thereby.

In some embodiments, the temperature of the heated substrate and/or air used to dehydrate the mixture is 20° C. or more above the temperature of the mixture before heating the mixture, but less than 100° C.

The mixture can be cooled by placing the mixture on a cooled substrate or surface (e.g., between about 5° ° C. to about 15° C.), cooling the substrate or surface on which the mixture has been placed (e.g., to between about 5° C. to about 15° C.) and/or bringing it into contact with a cold gas (e.g., air, nitrogen, or carbon dioxide having a temperature that is lower than the temperature of the mixture). When cooled, the temperature-dependent solubility limit of the salt in the mixture decreases until the mixture is ultimately supersaturated with the salt. The formation one or more salt crystals, preferably needle-shaped, is promoted by this. In some embodiments, the mixture is cooled by incubating it in a cold chamber with low humidity (e.g., temperatures between 0° C. and 10° C., relative humidity <40%)

The temperature in the mixture is preferably held above the dew point of the ambient air surrounding the mixture during the formation of the one or more salt crystals. This prevents the mixture becoming diluted with water condensed from the ambient air, which could lead to a decrease in the relative salt content in the mixture.

5.3.3. Crosslinking Conditions

The crosslinking conditions can be selected based upon the type of cross-linker used. For example, when using a cross-linker activated by ultraviolet light (e.g., benzophenone, a thioxanthone or a benzoin ether), the crosslinking conditions can comprise exposing the mixture to ultraviolet (UV) light. In some embodiments, UV light having a wavelength from about 250 nm to about 360 nm is used (e.g., 260±20 nm or 355±20 nm). The use of lower energy/longer wavelength UV light (e.g., 360 nm UV light vs. 254 nm UV light) can require longer exposure times. When using a cross-linker activated by visible light (e.g., ethyl eosin, eosin Y, rose bengal, camphorquinone or erythirosin), the crosslinking conditions can comprise exposing the mixture to visible light. When using a thermally activated cross-linker (e.g., 4,4' azobis(4-cyanopentanoic) acid, and 2,2-azobis[2-(2-imidazolin-2-yl) propane] dihydrochloride, or benzoyl peroxide), the crosslinking conditions can comprise exposing the mixture to heat.

The length and intensity of the crosslinking conditions can be selected to effect crosslinking of polymer molecules to other polymer molecules, crosslinking of polymer molecules to probe molecules (if present), and crosslinking of polymer molecules to substrate molecules or organic molecules present on the substrate (if present). The length and intensity of crosslinking conditions for a mixture containing probes can be determined experimentally to balance robustness of immobilization and nativity of probe molecules, for example.

5.3.4. Salt Crystal Dissolution

After crosslinking the polymer, the one or more salt crystals can be dissolved in the solvent in such a way that at least one channel is formed in the network, said channel extending starting from the surface and/or near the surface of the network into the interior of the network. Advantageously, after the salt crystals have dissolved in a solvent, a hollow, elongated channel is produced in the place where the salt crystal was, according to the principle of the "lost" form. The channels allow analytes to penetrate through the channel into the interior of the network and specifically bind a probe located in the interior of the network. When using an array produced by the method of the disclosure as a biological sensor, a high measurement accuracy and high measurement dynamic are permitted.

The solvent for dissolving the one or more salt crystals can be chosen in such a way that it is compatible to the polymer and probes, if present (e.g., the solvent can be chosen such that it does not dissolve the polymer and probes). Preferably, the solvent used is a water based buffer, such as diluted phosphate buffer. Methanol, ethanol, propanol or a mixture of these liquids can be added to the buffer to facilitate the removal of unbound polymer from the network.

After the removal of the salt crystals the network can collapse due to drying and can be rehydrated. Drying the network has advantages for shipping and stabilization of probe biomolecules.

5.3.5. Methods of Using the Three-Dimensional Networks

The networks and arrays of the disclosure can be used to determine the presence or absence of an analyte in a sample, preferably a liquid sample. The disclosure therefore provides methods for determining whether an analyte is present in a sample or plurality of samples, comprising contacting a network or array of the disclosure comprising probe molecules that are capable of binding to the analyte with the sample or plurality of samples and detecting binding of the analyte to the probe molecules, thereby determining whether the analyte is present in the sample or plurality of samples. When arrays comprising different species of probes capable of binding different species of analyte are used in the methods, the presence of the different species of analytes can be determined by detecting the binding of the different species of analytes to the probes. In some embodiments, the methods further comprise a step of quantifying the amount of analyte or analytes bound to the array.

The analyte can be, for example, a nucleic acid, such as a polymerase chain reaction (PCR) amplicon. In some embodiments, the PCR amplicon is amplified from a biological or environmental sample (e.g., blood, serum, plasma, tissue, cells, saliva, sputum, urine, cerebrospinal fluid, pleural fluid, milk, tears, stool, sweat, semen, whole cells, cell constituent, cell smear, or an extract or derivative thereof). In some embodiments, the nucleic acid is labeled (e.g., fluorescently labeled).

An analyte placed on the surface of the network can penetrate into the interior of the network through the channel in order to specifically bind to a probe (e.g., a biomolecule) covalently bonded there to the polymer. When using the arrays of the disclosure with the networks immobilized thereon as biological sensor, a high measurement accuracy and also a high measurement dynamic is permitted.

The networks and arrays of the disclosure can be regenerated after use as a biosensor and can be used several times (e.g., at 5 times, at least 10 times, at least 20 times, at least 30 times, at least 40 times, or at least 50 times). If the probe molecules are DNA, this can be achieved, for example, by heating the network(s) in an 1× phosphate buffered saline to a temperature between 80° C. and 90° C. for about 10 minutes. Then, the phosphate buffered saline can be exchanged for a new phosphate buffered saline to wash the denatured DNA out of the network(s). If the probe molecules of the network(s) or array are antigens the network(s) or array can be regenerated by bringing the network(s) into contact with 0.1 N NaOH for about 10 minutes. Then, the 0.1 N NaOH can be exchanged for a phosphate buffered saline to wash the antigens out of the network. Thus, some embodiments of the methods of using the networks and arrays of the disclosure comprise using a network or array that has been washed prior to contact with a sample or a plurality of samples.

5.4. Applications of Arrays of the Disclosure

Because the arrays of the invention achieve economical determination of the qualitative and quantitative presence of nucleic acids in a sample, it has immediate application to problems relating to health and disease in human and non-human animals.

In these applications a preparation containing a target molecule is derived or extracted from biological or environmental sources according to protocols known in the art. The target molecules can be derived or extracted from cells and tissues of all taxonomic classes, including viruses, bacteria and eukaryotes, prokaryotes, protista, plants, fungi, and animals of all phyla and classes. The animals can be vertebrates, mammals, primates, and especially humans. Blood, serum, plasma, tissue, cells, saliva, sputum, urine, cerebrospinal fluid, pleural fluid, milk, tears, stool, sweat, semen, whole cells, cell constituent, and cell smears are suitable sources of target molecules.

The target molecules are preferably nucleic acids amplified (e.g., by PCR) from any of the foregoing sources).

The arrays of the invention can include probes that are useful to detect pathogens of humans or non-human animals. Such probes include oligonucleotides complementary at least in part to bacterial, viral or fungal targets, or any combinations of bacterial, viral and fungal targets.

The arrays of the invention can include probes useful to detect gene expression in human or non-human animal cells, e.g., gene expression associated with a disease or disorder such as cancer, cardiovascular disease, or metabolic disease for the purpose of diagnosing a subject, monitoring treatment of a subject or prognosis of a subject's outcome. Gene expression information can then track disease progression or regression, and such information can assist in monitoring the success or changing the course of an initial therapy.

6. EXEMPLARY PROTOCOLS

The following exemplary protocols, which refer to the reference numbers provided in the figures, are within the scope of the disclosure and can be used in conjunction with the polymers, cross-linkers and probes of Sections 5.1.1, 5.1.2 and 5.1.4, respectively. Further useful polymers (including co-polymers) and cross-linker groups for use in the following methods are described in Rendl et al., 2011, Langmuir 27:6116-6123 and in US 2008/0293592, the contents of which are incorporated by reference herein. In one embodiment, a polymer mixture according to Section 7.1 is used.

6.1. Exemplary Protocol 1

Figure 2:
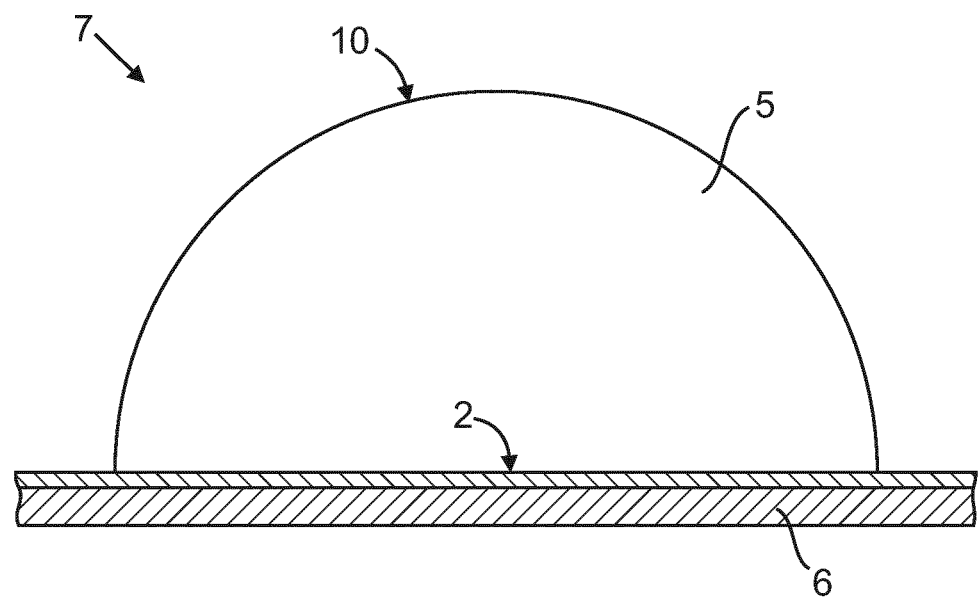
FIG. 2 shows shows a cross-section through a drop of the mixture (5) shown in FIG. 1 having a surface (10) located at a spot (7) of an organic surface (2) which is situated on a heated holder (6).
Figure 3:
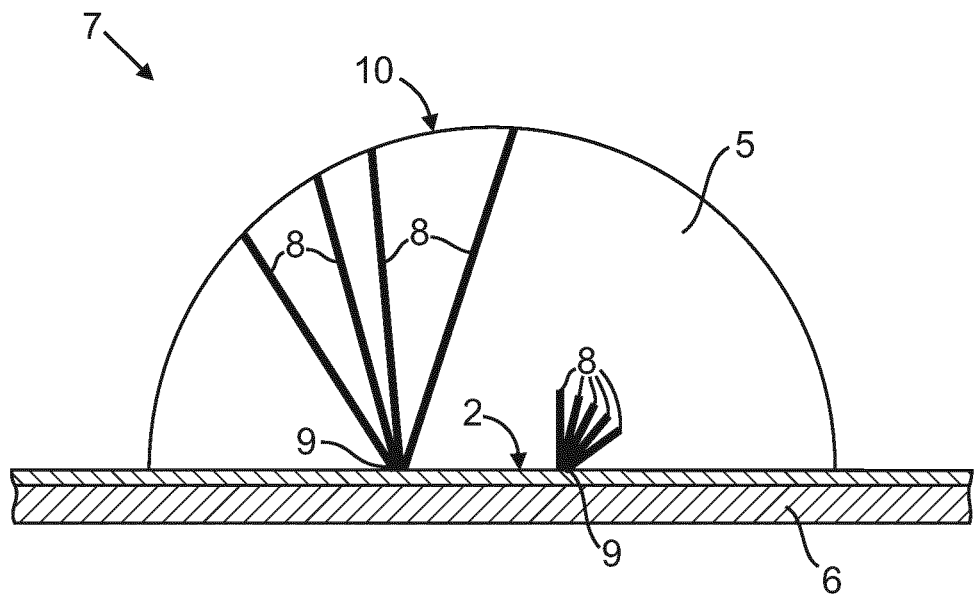
FIG. 3 shows shows a cross-section through the arrangement shown in FIG. 2 after the mixture has been heated and needle-shaped salt crystals (8) extending from crystallization germs (9) have been formed in the salt solution.
Figure 4:
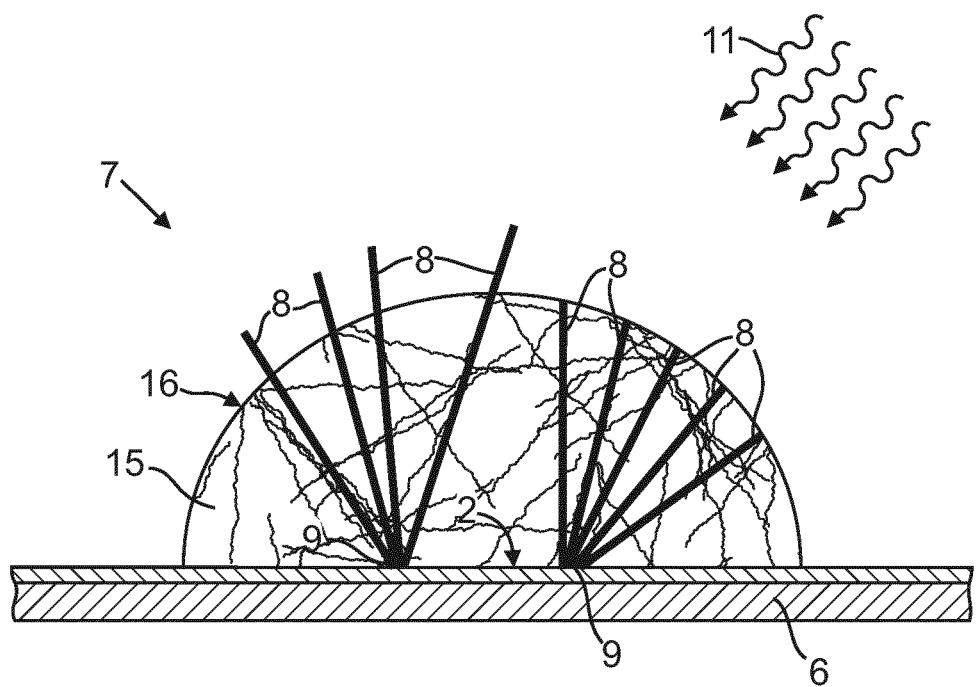
FIG. 4 shows shows a cross-section through the arrangement shown in FIG. 3 after the mixture has been dried and irradiated with optical radiation (11) to form a polymer network (15) having a surface (16).
Figure 5:
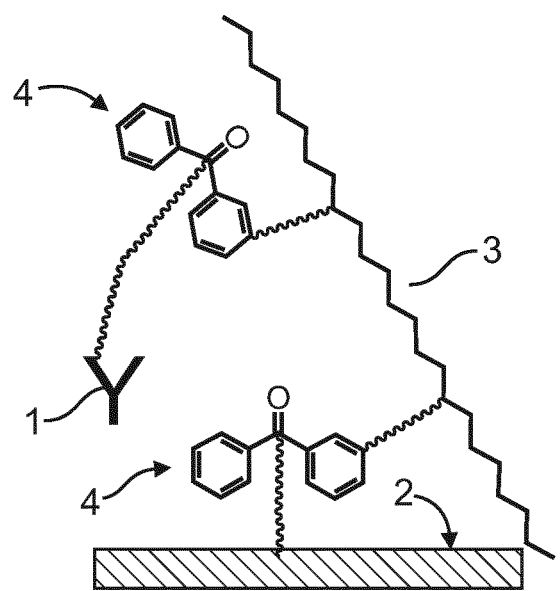
FIG. 5 shows shows a diagrammatic representation of the mixture of FIG. 1 following irradiation with optical radiation.

A plate with an organic surface (2) is placed on a heated holder (6). Temperatures between 50° C. and 70° ° C. are suitable. A mixture (5) containing a polymer (3), probe biomolecules (1) and an aqueous salt solution is spotted on the organic surface (2) using a standard DNA chip spotter (e.g., Scienion®, Germany). Volumes of 0.5 to 4 nl are printed on each spot (7) (see, FIG. 2). The liquid of these spots dries almost immediately leading to a very fast nucleation of salt crystals (8). After nucleation, needle-shaped salt crystals can extend from at least one crystallization germ (9) located in the volume of the mixture (5) to the surface (10) of the mixture (5) (see, FIG. 3). After nucleation of the crystals (8) the spots (7) are irradiated in a UV cross-linker immediately with optical UV radiation (11) (see, FIG. 4) such that the probe biomolecules (1) are covalently bonded to the polymer (3), and the polymer (3) is covalently bonded to the organic surface (2) and crosslinked (see, FIG. 5). Care is taken that the dried, crosslinked mixture (5) is not attracting moisture to become liquid again.

Figure 6:
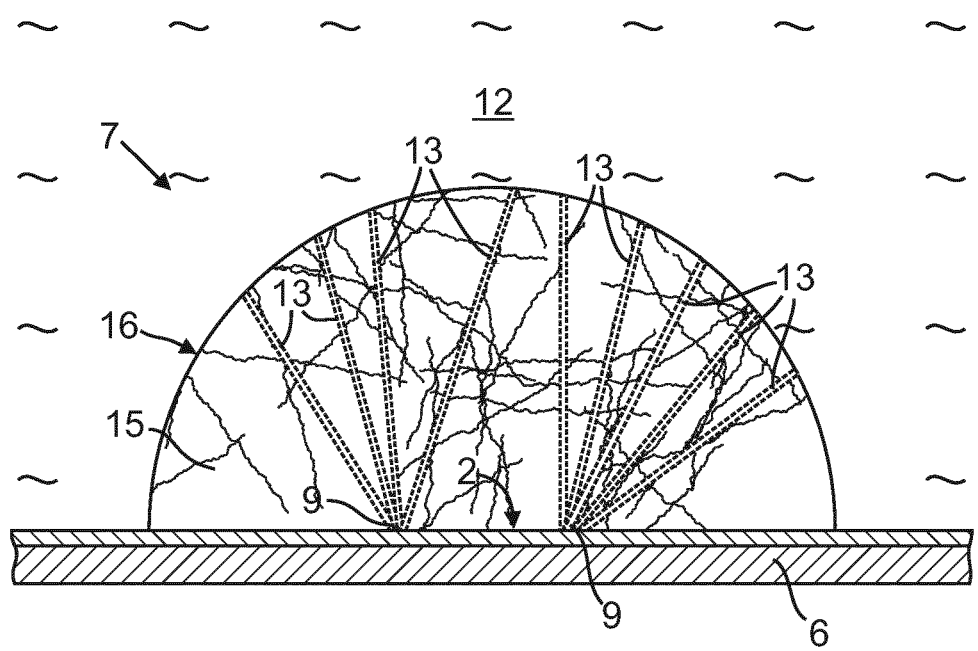
FIG. 6 shows shows a cross-section through the arrangement shown in FIG. 4 after dissolving the salt crystals in a solvent (12), forming channels (13).

The dried, crosslinked mixture (5) is then brought into contact with a solvent (12) for the crystals (8) such that at the places at which the crystals (8) were, channels (13) are formed in the network (15) comprising the polymer (3) and the probe biomolecules (1) (see, FIG. 6). Thereafter, the solvent (12) is removed. The channels (13) can extend from the surface (16) of the network (15) into the interior of the network (15). The solvent (12) in which the salt crystals (8) are dissolved is chosen in such a way that it is compatible to the probe biomolecule (1) and also the polymer (3). Preferably, the solvent (12) used is water based.

6.2. Exemplary Protocol 2

Figure 7:
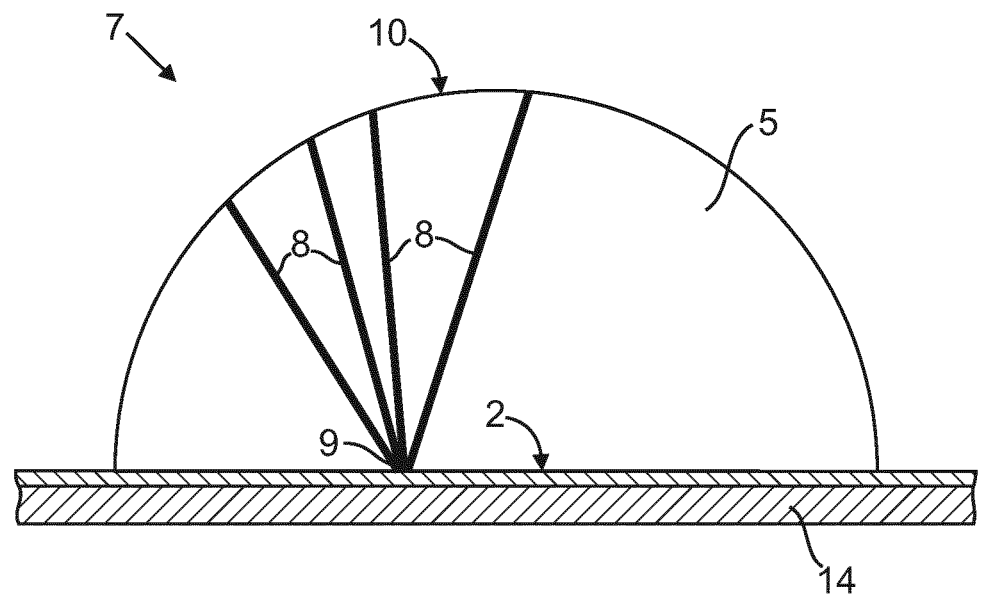
FIG. 7 shows a cross-section through the arrangement shown in FIG. 2 after the mixture has been cooled on a chilled holder (14) and needle-shaped salt crystals have been formed in the salt solution.
Figure 8:
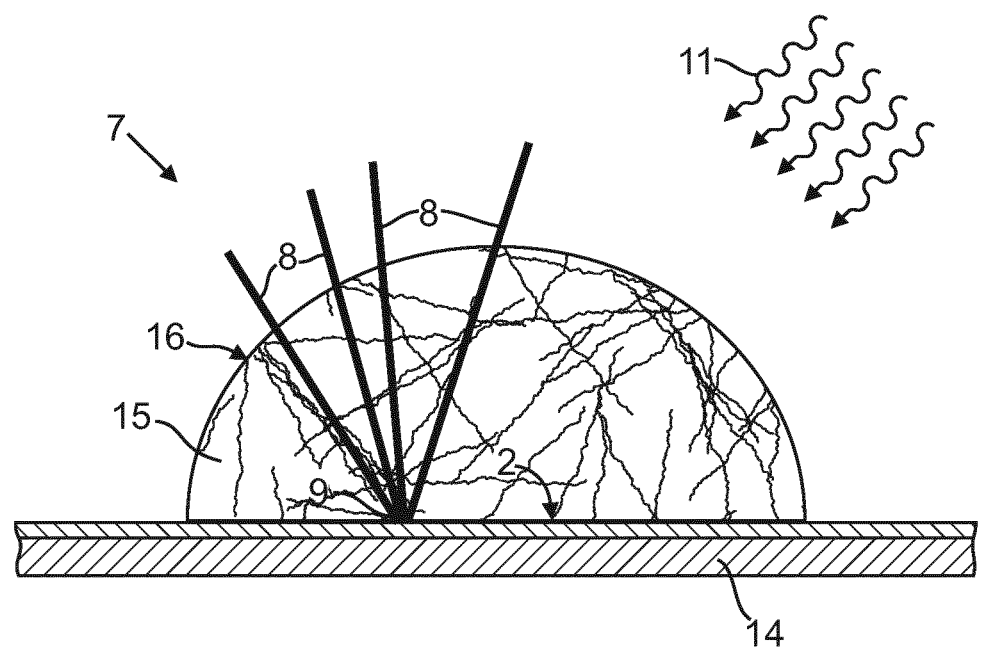
FIG. 8 shows shows a cross-section through the arrangement shown in FIG. 7 after the mixture has been dried and irradiated with optical irradiation.

A mixture (5) containing a polymer (3), probe biomolecules (1) and an aqueous salt solution is spotted on an organic surface (2) arranged on a plate using a standard DNA chip spotter (e.g., Scienion®, Germany). Volumes of 0.5 to 4 nl are printed on each spot 7 (see, FIG. 2). The plate with the spots (7) on the organic surface (2) is placed on a chilled holder (14) (see, FIG. 7). Temperatures between 5° C. and 15° C. are suitable. The liquid of these spots is cooled down to reach an over saturation of the buffer that almost immediately leads to a nucleation of crystals. After nucleation needle-shaped salt crystals (8) can extend from at least one crystallization germ (9) located in the volume of the mixture (5) to the surface (10) of the mixture (5). After printing these targets are put in an oven (e.g., at 70° C.) for complete drying. After nucleation of the crystals the spots are irradiated in a UV cross-linker immediately with optical UV radiation (11) (see, FIG. 8) such that the probe biomolecules (1) are covalently bonded to the polymer (3), and the polymer (3) is covalently bonded to the organic surface (2) and crosslinked. Care is taken that the dried, crosslinked mixture is not attracting moisture to become liquid again.

The dried, crosslinked mixture (5) is then brought into contact with a solvent (12) to dissolve the crystals (8) such that at the places at which the crystals (8) were, channels (13) are formed in the network (15) comprising the polymer (3) and the probe biomolecules (1). Thereafter, the solvent (12) is removed. The channels (13) can extend from the surface (16) of the network (15) into the interior of the network (15). The solvent (12) in which the salt crystals (8) are dissolved is chosen in such a way that it is compatible with the probe biomolecule (1) and the polymer (3). Preferably, the solvent (12) used is water based.

Figure 9:
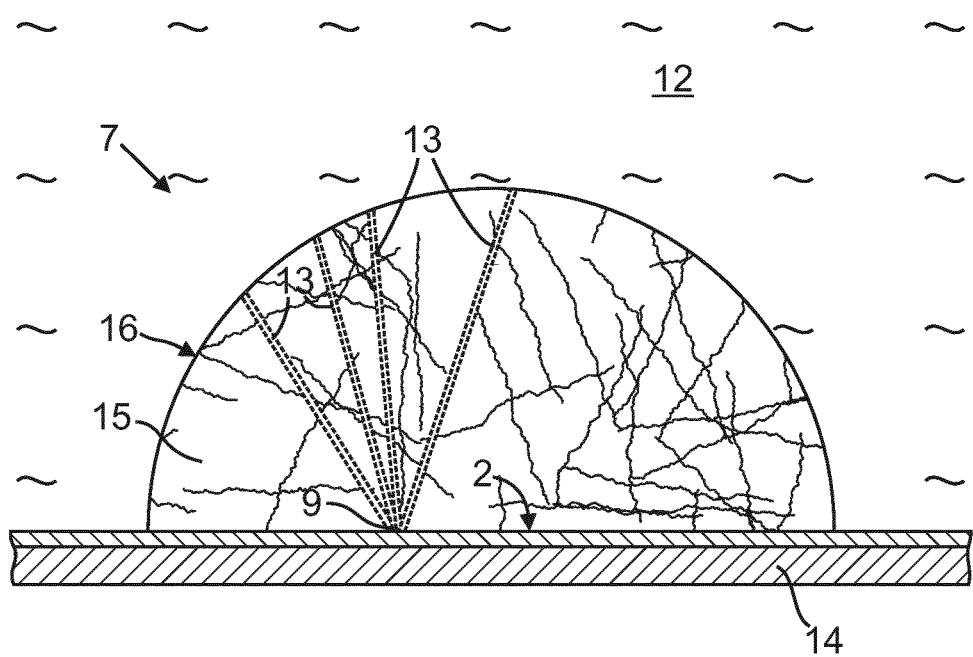
FIG. 9 shows shows a cross-section through the arrangement shown in FIG. 8 following dissolution of the salt crystals with a solvent.

As can be seen in FIG. 9 a plurality of channels (13) can be formed in the network (15). The channels (13) can extend from the surface (16) of the network (15) to at least one point located within the network (15). The channels (13) can be arranged in such a way that—starting from the surface (16) in the direction of the interior—the lateral distance between the channels (13) decreases.

6.3. Exemplary Protocol 3

A mixture (5) containing a polymer (3), probe biomolecules (1) and an aqueous salt solution is printed on an organic surface (2) of a plate at normal conditions with a humidity ranging from 40-80%, preferably 50-70%. The mixture can be near saturation, 400 mM sodium phosphate, pH 8, for example. Volumes of 0.5 to 4 nl are printed on each spot (7). The moisture content in the print compartment makes sure the spots (7) stay liquid without crystal formation (i.e., no nucleation takes place). The plate is then put in a container, a cardboard box for example. Lids are put on the plate having the organic surface (2) for transport. The plate with the spots (7) on the organic surface (2) is then put in a drying oven or on a hot plate to rapidly cause nucleation such that needle-shaped salt crystals (8) extend from at least one crystallization germ (9) located in the volume of the mixture toward the surface 10 of the mixture (5).

The temperature of the oven/hot plate should be 20° C. or more above the printing temperature. Temperatures above 100° C. are not necessary.

After drying, the mixture is irradiated to crosslink the polymer (3), probe biomolecules (1), and organic surface (2).

The dried, crosslinked mixture (5) is then brought into contact with a solvent (12) such that at the places at which the crystals (8) were, channels (13) are formed in the network (15) comprising the polymer (3) and the probe biomolecules (1). Thereafter, the solvent (12) is removed. The channels (13) can extend from the surface (16) of the network (15) into the interior of the network (15). The solvent (12) in which the salt crystals (8) are dissolved is chosen in such a way that it is compatible with the probe biomolecules (1) and the polymer (3). Preferably, the solvent (12) used is water based.

6.4. Exemplary Protocol 4

Alternatively, a plate with spots (7) on the organic surface (2) prepared as in exemplary protocol 3 can be cooled to achieve nucleation by putting in a cold chamber with low humidity (e.g., temperatures <10° C., relative humidity <40%). The drying can be performed by reducing the humidity or by applying a vacuum after nucleation has started. After nucleation, needle-shaped salt crystals (8) can extend from at least one crystallization germ (9) located in the volume of the mixture (5) toward the surface (10) of the mixture (5). The plate with the spots (7) on the organic surface (2) is put in an oven at 60°–70° C. for 1 hour to fully dry the spots. The spots (7) are UV irradiated with 1.00 J @ 254 nm in a UV cross-linker, i.e. Stratalinker® 2400. To do this, the plate with the spots (7) on the organic surface (2) can be put into the center of the chamber with the shorter side parallel to the door of the chamber. Then, the cover is removed and the cross-linker is started. When machine is finished the array is removed and the cover is replaced.

Alternatively, other UV cross-linkers with the same wavelength (240-270 nm, for example) or longer wavelengths, e.g., 360 nm, can be used.

The mixture (5) is then brought into contact with a solvent (12) to dissolve the crystals (8) such that at the places at which the crystals (8) were, channels (13) are formed in the network (15) comprising the polymer (3) and the probe biomolecules (1). Thereafter, the solvent (12) is removed. The channels (13) can extend from the surface (16) of the network (15) into the interior of the network (15). The solvent (12) in which the salt crystals (8) are dissolved is chosen in such a way that it is compatible with the probe biomolecules (1) the polymer (3). Preferably, the solvent (12) used is water based.

7. EXAMPLES

7.1. Example 1: Formation of a Three-Dimensional Polymer Network with Channels A 10 mg/ml polymer stock solution is prepared by dissolving 10 mg of the crosslinking polymer poly(dimethylacrylamide) co 5% methacryloyloxybenzophenone co 2.5% Sodium 4-vinylbenzenesulfonate in 1.0 ml of DNAse free water. This is achieved by vigorous shaking and vortexing for approximately 5 minutes until all the visible polymer is dissolved. The stock solution is then wrapped in foil to protect it from light and placed in a refrigerator overnight to ensure the polymer completely dissolves and to allow the foam to reduce. The polymer has at least two photoreactive groups per molecule.

A mixture comprising the polymer, DNA oligonucleotide probes, and sodium phosphate is made by mixing 10 µl of a 100 µM DNA oligonucleotide stock solution, 5 µl of the 10 mg/ml polymer stock solution (to provide a concentration of polymer in the mixture of 1 mg/ml), and 35 µl of a 500 mM sodium phosphate buffer, pH 8.

The mixture is used to prepare a three-dimensional network of the invention using the method of any one of Exemplary Protocols 1 through 4.

7.2. Example 2: Use of a Three-Dimensional Polymer Network to Detect Bacteria

7.2.1. Preparation of an Array of the Invention

Oligonucleotides for immobilization were dissolved at a concentration of 20 µM in a 400 mM sodium phosphate buffer, pH 7 containing 1 mg/ml of the photoreactive polymer described in Example 1. Each oligonucleotide had a length of 30-35 nucleotides complementary to the target DNA and a tail of 15 thymidines (for a total oligonucleotide length of 45-50 nucleotides).

The mixture was used to print the following spots on an organic surface of a plate to provide an array:

LL: So called landing lights. Cy5-labelled DNA oligonucleotide (0.2 µM), polymer and unlabeled oligonucleotide 19.8 µM to make up to 20 µM total oligonucleotide concentration.

GN: Oligonucleotide specific to gram negative bacteria.

GP: Oligonucleotide specific to gram positive bacteria.

S.Aure_1: Oligonucleotide specific to *Staphylococcus aureus* bacteria.

S.Aure_2: Oligonucleotide specific to *Staphylococcus aureus* bacteria.

E. coli_1: Oligonucleotide specific to *Escherichia coli* bacteria.

E. coli_2: Oligonucleotide specific to *Escherichia coli* bacteria.

In order to avoid the formation of salt crystals on the source plate (i.e., the plate from which the mixture was taken) this plate was kept at ambient temperature (22° C.).

A Greiner 96 well plate with a flat crystal clear bottom with an organic surface was cooled to 10° C. to avoid drying out of the printed spots. Using a Scienion® SciFlex 5 printer with a PDC 90 nozzle 8 drops per spot were printed on the organic surface, resulting in a spot volume of approx. 1.4 nl. The humidity of the printer was kept at 60-65% relative humidity.

After the print the size of the spots was checked by an automated head camera on the print head to assure that no drying in or crystal formation has taken place in the spots. All spots were still wet and have the same size. No crystal formation was visible.

The 96 well plate was then sealed with a lid to avoid drying in and immediately put on a hot plate (70° C.) in a drying oven to perform crystal initiation and drying of the spots.

After 1 hr incubation at 70° C. to ensure proper drying of the spots the plate was irradiated with 1J @ 254 nm in a Stratalinker® 2000.

7.2.2. Preparation of a Control Array

A procedure similar to that described in Section 7.2.1 was used but the target plate was kept at ambient temperature substantially as described by Rendl et al., 2011, Langmuir 27:6116-6123. After the print, some spots showed a reduced size, i.e., some of the spots in random places in the array were dried in and exhibited phase separation immediately after the printing. The plate was then taken out of the printer and taken to the sample drying process as described above with no lid on, upon which further drying in occurred.

7.2.3. Hybridization Assay

Before use the plates were washed in a plate washer for 3 times with 300 µl of wash buffer (100 mM sodium phosphate pH 7) and then the buffer was exchanged to 1 mM sodium phosphate pH 7. The plates were heated for 10 minutes at 90° C. on a heater shaker to extract unbound DNA and polymer. The buffer then was exchanged to 100 mM sodium phosphate buffer using an automated 96 well plate washer.

A mix of 20 ml Cy5-labeled PCR product and 30 ml sodium phosphate buffer (250 mM, pH7) was incubated on the arrays for 10 minutes at 80° C. and 30 minutes at 55° C. on heater shaker. Afterward the plates were washed with 100 mM sodium phosphate buffer pH7 for three times in 96 well plate washer. Plates with buffer were scanned in Sensovation® Flair reader and the spot intensity of the different spots was measured.

7.2.4. Results 8 arrays produced by the method of Section 7.2.1 and 8 arrays produced by the method of Section 7.2.2 were analysed and the data processed in a spreadsheet program. Mean and standard error of the mean (SEM) were calculated and compared. Results are shown in FIGS. 14-16.

8. Example 3: Reusability of a Three-Dimensional Polymer Network Array

Several arrays were prepared according to the procedure described in Section 7.2.1, including a "landing light" spot containing fluorescently labeled oligonucleotides. The arrays were reused in hybridization assays and washed according to the following procedure in between hybridizations:
 (a) the arrays were washed three times with 100 mM phosphate buffer pH 7;
 (b) the buffer was then exchanged to 1 mM phosphate buffer pH 7; and
 (c) the arrays were then heated to 80° C. and washed while hot with 100 mM phosphate buffer pH 7.

The strength of the fluorescent signal from the landing light spot was determined in between uses. After 10 uses, the fluorescent signal lost less than 25% of its intensity. The arrays were reused until a reference spot hybridized with a reference DNA (internal control) showed a loss of signal of 50%.

9. SPECIFIC EMBODIMENTS

The present disclosure is exemplified by the specific embodiments below.

1. A three-dimensional network having a surface and an interior comprising (a) a crosslinked polymer, (b) one or more channels, and (c) optionally, probe molecules immobilized in the network, said three-dimensional network optionally covalently attached to the surface of a substrate.

2. The three-dimensional network of embodiment 1, wherein at least one of the one or more channels extends into the interior from a point that is less than 10 microns from the surface of the network.

3. The three-dimensional network of embodiment 2, wherein at least one of the one or more channels extends into the interior from a point that is less than 9 microns from the surface of the network.

4. The three-dimensional network of embodiment 3, wherein at least one of the one or more channels extends into the interior from a point that is less than 8 microns from the surface of the network.

5. The three-dimensional network of embodiment 4, wherein at least one of the one or more channels extends into the interior from a point that is less than 7 microns from the surface of the network.

6. The three-dimensional network of embodiment 5, wherein at least one of the one or more channels extends into the interior from a point that is less than 6 microns from the surface of the network.

7. The three-dimensional network of embodiment 6, wherein at least one of the one or more channels extends into the interior from a point that is less than 5 microns from the surface of the network.

8. The three-dimensional network of embodiment 7, wherein at least one of the one or more channels extends into the interior from a point that is less than 4 microns from the surface of the network.

9. The three-dimensional network of embodiment 8, wherein at least one of the one or more channels extends into the interior from a point that is less than 3 microns from the surface of the network.

10. The three-dimensional network of embodiment 9, wherein at least one of the one or more channels extends into the interior from a point that is less than 2 microns from the surface of the network.

11. The three-dimensional network of embodiment 10, wherein at least one of the one or more channels extends into the interior from a point that is less than 1 micron from the surface of the network.

12. The three-dimensional network of embodiment 11, wherein at least one of the one or more channels extends into the interior from a point on the surface of the network.

13. The three-dimensional network of any one of embodiments 1 to 12, wherein at least one of the one or more channels has a length that is at least 10% of the largest dimension of the network.

14. The three-dimensional network of embodiment 13, wherein at least one of the one or more channels has a length that is 10% to 100% of the largest dimension of the network.

15. The three-dimensional network of embodiment 13 or embodiment 14, wherein at least one of the one or more channels has a length that is at least 15% of the largest dimension of the network.

16. The three-dimensional network of embodiment 13 or embodiment 14, wherein at least one of the one or more channels has a length that is at least 20% of the largest dimension of the network.

17. The three-dimensional network of embodiment 13 or embodiment 14 wherein at least one of the one or more channels has a length that is at least 25% of the largest dimension of the network.

18. The three-dimensional network of embodiment 13 or embodiment 14, wherein at least one of the one or more channels has a length that is 10% to 90% of the largest dimension of the network.

19. The three-dimensional network of embodiment 13 or embodiment 14, wherein at least one of the one or more channels has a length that is 10% to 80% of the largest dimension of the network.

20. The three-dimensional network of embodiment 13 or embodiment 14, wherein at least one of the one or more channels has a length that is 10% to 70% of the largest dimension of the network.

21. The three-dimensional network of embodiment 13 or embodiment 14, wherein at least one of the one or more channels has a length that is 10% to 60% of the largest dimension of the network.

22. The three-dimensional network of embodiment 13 or embodiment 14, wherein at least one of the one or more channels has a length that is 10% to 50% of the largest dimension of the network 23. The three-dimensional network of embodiment 13 or embodiment 14, wherein at least one of the one or more channels has a length that is 10% to 40% of the largest dimension of the network 24. The three-dimensional network of embodiment 13 or embodiment 14, wherein at least one of the one or more channels has a length that is 10% to 30% of the largest dimension of the network.

25. The three-dimensional network of embodiment 13 or embodiment 14, wherein at least one of the one or more channels has a length that is 10% to 25% of the largest dimension of the network 26. The three-dimensional network of embodiment 13 or embodiment 14, wherein at least one of the one or more channels has a length that is 10% to 20% of the largest dimension of the network 27. The three-dimensional network of embodiment 13 or embodiment 14, wherein at least one of the one or more channels has a length that is 10% to 15% of the largest dimension of the network.

28. The three-dimensional network of embodiment 13 or embodiment 14, wherein at least one of the one or more channels has a length that is 15% to 20% of the largest dimension of the network.

29. The three-dimensional network of embodiment 13 or embodiment 14, wherein at least one of the one or more channels has a length that is 15% to 25% of the largest dimension of the network.

30. The three-dimensional network of embodiment 13 or embodiment 14, wherein at least one of the one or more channels has a length that is 15% to 35% of the largest dimension of the network.

31. The three-dimensional network of embodiment 13 or embodiment 14, wherein at least one of the one or more channels has a length that is 20% to 25% of the largest dimension of the network.

32. The three-dimensional network of embodiment 13 or embodiment 14, wherein at least one of the one or more channels has a length that is 25% to 30% of the largest dimension of the network.

33. The three-dimensional network of any one of embodiments 1 to 32, wherein at least one of the one or more channels has a minimum cross-section of at least 5 times the network's mesh size.

34. The three-dimensional network of embodiment 33, wherein at least one of the one or more channels has a minimum cross-section of at least 10 times the network's mesh size.

35. The three-dimensional network of embodiment 34, wherein at least one of the one or more channels has a minimum cross-section of at least 15 times the network's mesh size.

36. The three-dimensional network of embodiment 35, wherein at least one of the one or more channels has a minimum cross-section of at least 20 times the network's mesh size.

37. The three-dimensional network of embodiment 33, wherein at least one of the one or more channels has a minimum cross-section of 5 to 10 times the network's mesh size.

38. The three-dimensional network of embodiment 33, wherein at least one of the one or more channels has a minimum cross-section of 5 to 15 times the network's mesh size.

39. The three-dimensional network of embodiment 33, wherein at least one of the one or more channels has a minimum cross-section of 5 to 20 times the network's mesh size.

40. The three-dimensional network of embodiment 33, wherein at least one of the one or more channels has a minimum cross-section of 5 to 25 times the network's mesh size.

41. The three-dimensional network of embodiment 33, wherein at least one of the one or more channels has a minimum cross-section of 5 to 30 times the network's mesh size.

42. The three-dimensional network of embodiment 33, wherein at least one of the one or more channels has a minimum cross-section of 10 to 15 times the network's mesh size.

43. The three-dimensional network of embodiment 33, wherein at least one of the one or more channels has a minimum cross-section of 10 to 20 times the network's mesh size.

44. The three-dimensional network of embodiment 33, wherein at least one of the one or more channels has a minimum cross-section of 10 to 25 times the network's mesh size.

45. The three-dimensional network of embodiment 33, wherein at least one of the one or more channels has a minimum cross-section of 10 to 30 times the network's mesh size.

46. The three-dimensional network of embodiment 33, wherein at least one of the one or more channels has a minimum cross-section of 15 to 20 times the network's mesh size.

47. The three-dimensional network of embodiment 33, wherein at least one of the one or more channels has a minimum cross-section of 15 to 25 times the network's mesh size.

48. The three-dimensional network of embodiment 33, wherein at least one of the one or more channels has a minimum cross-section of 15 to 30 times the network's mesh size.

49. The three-dimensional network of embodiment 33, wherein at least one of the one or more channels has a minimum cross-section of 20 to 25 times the network's mesh size.

50. The three-dimensional network of embodiment 33, wherein at least one of the one or more channels has a minimum cross-section of 20 to 30 times the network's mesh size.

51. The three-dimensional network of embodiment 33, wherein at least one of the one or more channels has a minimum cross-section of 25 to 30 times the network's mesh size.

52. The three-dimensional network of any one of embodiments 1 to 51, comprising a plurality of channels.

53. The three-dimensional network of embodiment 52, wherein the plurality of channels is at least 5 channels.

54. The three-dimensional network of embodiment 53, wherein the plurality of channels is at least 10 channels.

55. The three-dimensional network of embodiment 54, wherein the plurality of channels is at least 15 channels.

56. The three-dimensional network of any one of embodiments 52 to 55, wherein the plurality of channels is up to 50 channels.

57. The three-dimensional network of embodiment 52, wherein the plurality of channels is 10 to 50 channels.

58. The three-dimensional network of any one of embodiments 52 to 57, wherein a plurality of channels converge at a point in the interior of the network such that the lateral distance between the channels decreases from the surface toward the point in the interior.

59. The three dimensional network of embodiment 58, wherein the plurality of channels are connected at their point of convergence.

60. The three dimensional network of embodiment 58, wherein a majority of channels in the network converge at one or more points in the interior of the network such that the lateral distance between the channels decreases from the surface toward the point in the interior.

61. The three dimensional network of embodiment 60, wherein a plurality of channels that converge at the same point in the interior of the network are connected at their point of convergence.

62. The three dimensional network of embodiment 60, wherein the majority of channels in the network are connected to other channels at one or more convergence points in the network.

63. The three-dimensional network of any one of embodiments 52 to 62, wherein at least a plurality of channels, or wherein a majority of the channels in the network, extend into the interior from a point that is less than 10 microns from the surface of the network.

64. The three-dimensional network of embodiment 63, wherein at least a plurality of channels, or wherein a majority of the channels in the network, extend into the interior from a point that is less than 9 microns from the surface of the network.

65. The three-dimensional network of embodiment 64, wherein at least a plurality of channels, or wherein a majority of the channels in the network, extend into the interior from a point that is less than 8 microns from the surface of the network.

66. The three-dimensional network of embodiment 65 wherein at least a plurality of channels, or wherein a majority of the channels in the network, extend into the interior from a point that is less than 7 microns from the surface of the network.

67. The three-dimensional network of embodiment 66, wherein at least a plurality of channels, or wherein a majority of the channels in the network, extend into the interior from a point that is less than 6 microns from the surface of the network.

68. The three-dimensional network of embodiment 67, wherein at least a plurality of channels, or wherein a majority of the channels in the network, extend into the interior from a point that is less than 5 microns from the surface of the network.

69. The three-dimensional network of embodiment 68, wherein at least a plurality of channels, or wherein a majority of the channels in the network, extend into the interior from a point that is less than 4 microns from the surface of the network.

70. The three-dimensional network of embodiment 69, wherein at least a plurality of channels, or wherein a majority of the channels in the network, extend into the interior from a point that is less than 3 microns from the surface of the network.

71. The three-dimensional network of embodiment 70, wherein at least a plurality of channels, or wherein a majority of the channels in the network, extend into the interior from a point that is less than 2 microns from the surface of the network.

72. The three-dimensional network of embodiment 71, wherein at least a plurality of channels, or wherein a majority of the channels in the network, extend into the interior from a point that is less than 1 micron from the surface of the network.

73. The three-dimensional network of embodiment 72, wherein at least a plurality of channels, or wherein a majority of the channels in the network, extend into the interior from a point on the surface of the network.

74. The three-dimensional network of any one of embodiments 52 to 73, wherein at least a plurality of channels, or wherein a majority of the channels in the network, have a length that is at least 10% of the largest dimension of the network.

75. The three-dimensional network of embodiment 74, wherein at least a plurality of channels, or wherein a majority of the channels in the network, have a length that is 10% to 100% of the largest dimension of the network.

76. The three-dimensional network of embodiment 74 or embodiment 75, wherein at least a plurality of channels, or wherein a majority of the channels in the network, have a length that is at least 15% of the largest dimension of the network.

77. The three-dimensional network of embodiment 74 or embodiment 75, wherein at least a plurality of channels, or wherein a majority of the channels in the network, have a length that is at least 20% of the largest dimension of the network.

78. The three-dimensional network of embodiment 74 or embodiment 75, wherein at least a plurality of channels, or wherein a majority of the channels in the network, have a length that is at least 25% of the largest dimension of the network.

79. The three-dimensional network of embodiment 74 or embodiment 75, wherein at least a plurality of channels, or wherein a majority of the channels in the network, have a length that is 10% to 90% of the largest dimension of the network.

80. The three-dimensional network of embodiment 74 or embodiment 75, wherein at least a plurality of channels, or wherein a majority of the channels in the network, have a length that is 10% to 80% of the largest dimension of the network.

81. The three-dimensional network of embodiment 74 or embodiment 75, wherein at least a plurality of channels, or wherein a majority of the channels in the network, have a length that is 10% to 70% of the largest dimension of the network.

82. The three-dimensional network of embodiment 74 or embodiment 75, wherein at least a plurality of channels, or wherein a majority of the channels in the network, have a length that is 10% to 60% of the largest dimension of the network.

83. The three-dimensional network of embodiment 74 or embodiment 75, wherein at least a plurality of channels, or wherein a majority of the channels in the network, have a length that is 10% to 50% of the largest dimension of the network 84. The three-dimensional network of embodiment 74 or embodiment 75, wherein at least a plurality of channels, or wherein a majority of the channels in the network, have a length that is 10% to 40% of the largest dimension of the network 85. The three-dimensional network of embodiment 74 or embodiment 75, wherein at least a plurality of channels, or wherein a majority of the channels in the network, have a length that is 10% to 30% of the largest dimension of the network.

86. The three-dimensional network of embodiment 74 or embodiment 75, wherein at least a plurality of channels, or wherein a majority of the channels in the network, have a length that is 10% to 25% of the largest dimension of the network 87. The three-dimensional network of embodiment 74 or embodiment 75, wherein at least a plurality of channels, or wherein a majority of the channels in the network, have a length that is 10% to 20% of the largest dimension of the network 88. The three-dimensional network of embodiment 74 or embodiment 75, wherein at least a plurality of channels, or wherein a majority of the channels in the network, have a length that is 10% to 15% of the largest dimension of the network.

89. The three-dimensional network of embodiment 74 or embodiment 75, wherein at least a plurality of channels, or wherein a majority of the channels in the network, have a length that is 15% to 20% of the largest dimension of the network.

90. The three-dimensional network of embodiment 74 or embodiment 75, wherein at least a plurality of channels, or wherein a majority of the channels in the network, have a length that is 15% to 25% of the largest dimension of the network.

91. The three-dimensional network of embodiment 74 or embodiment 75, wherein at least a plurality of channels, or wherein a majority of the channels in the network, have a length that is 15% to 30% of the largest dimension of the network.

92. The three-dimensional network of embodiment 74 or embodiment 75, wherein at least a plurality of channels, or wherein a majority of the channels in the network, have a length that is 20% to 25% of the largest dimension of the network.

93. The three-dimensional network of embodiment 74 or embodiment 75, wherein at least a plurality of channels, or wherein a majority of the channels in the network, have a length that is 25% to 30% of the largest dimension of the network.

94. The three-dimensional network of any one of embodiments 52 to 93, wherein at least a plurality of channels, or wherein a majority of the channels in the network, have a minimum cross-section of at least 5 times the network's mesh size.

95. The three-dimensional network of embodiment 94, wherein at least a plurality of channels, or wherein a majority of the channels in the network, have a minimum cross-section of at least 10 times the network's mesh size.

96. The three-dimensional network of embodiment 95, wherein at least a plurality of channels, or wherein a majority of the channels in the network, have a minimum cross-section of at least 15 times the network's mesh size.

97. The three-dimensional network of embodiment 96, wherein at least a plurality of channels, or wherein a majority of the channels in the network, have a minimum cross-section of at least 20 times the network's mesh size.

98. The three-dimensional network of embodiment 94, wherein at least a plurality of channels, or wherein a majority of the channels in the network, have a minimum cross-section of 5 to 10 times the network's mesh size.

99. The three-dimensional network of embodiment 94, wherein at least a plurality of channels, or wherein a majority of the channels in the network, have a minimum cross-section of 5 to 15 times the network's mesh size.

100. The three-dimensional network of embodiment 94, wherein at least a plurality of channels, or wherein a majority of the channels in the network, have a minimum cross-section of 5 to 20 times the network's mesh size.

101. The three-dimensional network of embodiment 94, wherein at least a plurality of channels, or wherein a majority of the channels in the network, have a minimum cross-section of 5 to 25 times the network's mesh size.

102. The three-dimensional network of embodiment 94, wherein at least a plurality of channels, or wherein a majority of the channels in the network, have a minimum cross-section of 5 to 30 times the network's mesh size.

103. The three-dimensional network of embodiment 94, wherein at least a plurality of channels, or wherein a majority of the channels in the network, have a minimum cross-section of 10 to 15 times the network's mesh size.

104. The three-dimensional network of embodiment 94, wherein at least a plurality of channels, or wherein a majority of the channels in the network, have a minimum cross-section of 10 to 20 times the network's mesh size.

105. The three-dimensional network of embodiment 94, wherein at least a plurality of channels, or wherein a majority of the channels in the network, have a minimum cross-section of 10 to 25 times the network's mesh size.

106. The three-dimensional network of embodiment 94, wherein at least a plurality of channels, or wherein a majority of the channels in the network, have a minimum cross-section of 10 to 30 times the network's mesh size.

107. The three-dimensional network of embodiment 94, wherein at least a plurality of channels, or wherein a majority of the channels in the network, have a minimum cross-section of 15 to 20 times the network's mesh size.

108. The three-dimensional network of embodiment 94, wherein at least a plurality of channels, or wherein a majority of the channels in the network, have a minimum cross-section of 15 to 25 times the network's mesh size.

109. The three-dimensional network of embodiment 94, wherein at least a plurality of channels, or wherein a majority of the channels in the network, have a minimum cross-section of 15 to 30 times the network's mesh size.

110. The three-dimensional network of embodiment 94, wherein at least a plurality of channels, or wherein a majority of the channels in the network, have a minimum cross-section of 20 to 25 times the network's mesh size.

111. The three-dimensional network of embodiment 94, wherein at least a plurality of channels, or wherein a majority of the channels in the network, have a minimum cross-section of 20 to 30 times the network's mesh size.

112. The three-dimensional network of embodiment 94, wherein at least a plurality of channels, or wherein a majority of the channels in the network, have a minimum cross-section of 25 to 30 times the network's mesh size.

113. The three-dimensional network of any one of embodiments 1 to 112, wherein the network has a mesh size of 5 nm to 75 nm in its hydrated state.

114. The three-dimensional network of embodiment 113, wherein the network has a mesh size of 10 nm to 50 nm in its hydrated state.

115. The three-dimensional network of embodiment 113, wherein the network has a mesh size of 10 nm to 40 nm in its hydrated state.

116. The three-dimensional network of embodiment 113, wherein the network has a mesh size of 10 nm to 30 nm in its hydrated state.

117. The three-dimensional network of embodiment 113, wherein the network has a mesh size of 10 nm to 20 nm in its hydrated state.

118. The three-dimensional network of embodiment 113, wherein the network has a mesh size of 20 nm to 50 nm in its hydrated state.

119. The three-dimensional network of embodiment 113, wherein the network has a mesh size of 20 nm to 40 nm in its hydrated state.

120. The three-dimensional network of embodiment 113, wherein the network has a mesh size of 20 nm to 30 nm in its hydrated state.

121. The three-dimensional network of embodiment 113, wherein the network has a mesh size of 30 nm to 50 nm in its hydrated state.

122. The three-dimensional network of embodiment 113, wherein the network has a mesh size of 30 nm to 40 nm in its hydrated state.

123. The three-dimensional network of embodiment 113, wherein the network has a mesh size of 40 nm to 50 nm in its hydrated state.

124. The three-dimensional network of any one of embodiments 1 to 123, wherein the crosslinked polymer is a water-swellable polymer.

125. The three-dimensional network of embodiment 124, wherein the water-swellable polymer can absorb up to 50 times its weight of deionized, distilled water.

126. The three-dimensional network of embodiment 124 or embodiment 125, wherein the water-swellable polymer can absorb 5 to 50 times its own volume of deionized, distilled water.

127. The three-dimensional network of any one of embodiments 124 to 126, wherein the water-swellable polymer can absorb up to 30 times its weight of saline.

128. The three-dimensional network of any one of embodiments 124 to 127, wherein the water-swellable polymer can absorb 4 to 30 times its own volume of saline.

129. The three-dimensional network of any one of embodiments 1 to 128, wherein the crosslinked polymer comprises a crosslinked homopolymer.

130. The three-dimensional network of any one of embodiments 1 to 128, wherein the crosslinked polymer comprises a crosslinked copolymer.

131. The three-dimensional network of any one of embodiments 1 to 128, wherein the crosslinked polymer comprises a crosslinked mixture of a homopolymer and a copolymer.

132. The three-dimensional network of any one of embodiments 129 to 131, wherein the crosslinked polymer comprises a polymer polymerized from one or more species of monomers.

133. The three-dimensional network of embodiment 132, wherein each species of monomer comprises a polymerizable group independently selected from an acrylate group, a methacrylate group, an ethacrylate group, a 2-phenyl acrylate group, an acrylamide group, a methacrylamide group, an itaconate group, and a styrene group.

134. The three-dimensional network of embodiment 133, wherein at least one monomer species in the polymer comprises a methacrylate group.

135. The three-dimensional network of embodiment 134, wherein the at least one monomer species comprising a methacrylate group is methacryloyloxybenzophenone (MABP).

136. The three-dimensional network of embodiment 132, wherein the crosslinked polymer comprises a polymer polymerized from dimethylacrylamide (DMAA), methacryloyloxybenzophenone (MABP), and sodium 4-vinylbenzenesulfonate (SSNa).

137. The three-dimensional network of any one of embodiments 1 to 136, wherein the probe molecules are covalently attached to the network.

138. The three-dimensional network of any one of embodiments 1 to 137, wherein a majority of probe molecules are immobilized in the interior of the network.

139. The three-dimensional network of embodiment 138, wherein at least a portion of the probe molecules adjoin a channel.

140. In various embodiments, the probe density it at least 10%, at least 20%, at least 30%, at least 40%, or at least 50% more dense at the interface between the polymer and the channels than within regions of the polymer not adjacent to a channel.

141. The three-dimensional network of any one of embodiments 1 to 139, wherein the probe density at the interface between the polymer and the channels is on average at least 10% greater than within regions of the polymer not abutting a channel.

142. The three-dimensional network of embodiment 140, wherein the probe density at the interface between the polymer and the channels is on average at least 20% greater than within regions of the polymer not abutting a channel.

143. The three-dimensional network of embodiment 140, wherein the probe density at the interface between the polymer and the channels is on average at least 30% greater than within regions of the polymer not abutting a channel.

144. The three-dimensional network of embodiment 140, wherein the probe density at the interface between the polymer and the channels is on average at least 40% greater than within regions of the polymer not abutting a channel.

145. The three-dimensional network of embodiment 140, wherein the probe density at the interface between the polymer and the channels is on average at least 50% greater than within regions of the polymer not abutting a channel.

146. The three-dimensional network of any one of embodiments 1 to 145, wherein the probe molecules comprise a nucleic acid, a nucleic acid derivative, a peptide, a polypeptide, a protein, a carbohydrate, a lipid, a cell, a ligand, or a combination thereof, preferably wherein the probe molecules comprise a nucleic acid or a nucleic acid derivative.

147. The three-dimensional network of any one of embodiments 1 to 146, wherein the probe molecules comprise an antibody, an antibody fragment, an antigen, an epitope, an enzyme, an enzyme substrate, an enzyme inhibitor, a nucleic acid, or a combination thereof.

148. The three-dimensional network of any one of embodiments 1 to 147, wherein the probe molecules comprise a nucleic acid.

149. The three-dimensional network of embodiment 148, wherein the nucleic acid is an oligonucleotide.

150. The three-dimensional network of embodiment 149, wherein the oligonucleotide is 12 to 30 nucleotides long.

151. The three-dimensional network of embodiment 149, wherein the oligonucleotide is 14 to 30 nucleotides long.

152. The three-dimensional network of embodiment 149, wherein the oligonucleotide is 14 to 25 nucleotides long.

153. The three-dimensional network of embodiment 149, wherein the oligonucleotide is 14 to 20 nucleotides long.

154. The three-dimensional network of embodiment 149, wherein the oligonucleotide is 15 to 30 nucleotides long.

155. The three-dimensional network of embodiment 149, wherein the oligonucleotide is 15 to 25 nucleotides long.

156. The three-dimensional network of embodiment 149, wherein the oligonucleotide is 15 to 20 nucleotides long.

157. The three-dimensional network of embodiment 149, wherein the oligonucleotide is 16 to 30 nucleotides long.

158. The three-dimensional network of embodiment 149, wherein the oligonucleotide is 16 to 25 nucleotides long.

159. The three-dimensional network of embodiment 149, wherein the oligonucleotide is 16 to 20 nucleotides long.

160. The three-dimensional network of embodiment 149, wherein the oligonucleotide is 15 to 40 nucleotides long.

161. The three-dimensional network of embodiment 149, wherein the oligonucleotide is 15 to 45 nucleotides long.

162. The three-dimensional network of embodiment 149, wherein the oligonucleotide is 15 to 50 nucleotides long.

163. The three-dimensional network of embodiment 149, wherein the oligonucleotide is 15 to 60 nucleotides long.

164. The three-dimensional network of embodiment 149, wherein the oligonucleotide is 20 to 55 nucleotides long.

165. The three-dimensional network of embodiment 149, wherein the oligonucleotide is 18 to 60 nucleotides long.

166. The three-dimensional network of embodiment 149, wherein the oligonucleotide is 20 to 50 nucleotides long.

167. The three-dimensional network of embodiment 149, wherein the oligonucleotide is 30 to 90 nucleotides long.

168. The three-dimensional network of embodiment 149, wherein the oligonucleotide is 20 to 100 nucleotides long.

169. The three-dimensional network of embodiment 149, wherein the oligonucleotide is 20 to 60 nucleotides long.

170. The three-dimensional network of embodiment 149, wherein the oligonucleotide is 40 to 80 nucleotides long.

171. The three-dimensional network of embodiment 149, wherein the oligonucleotide is 40 to 100 nucleotides long.

172. The three-dimensional network of embodiment 149, wherein the oligonucleotide is 20 to 120 nucleotides long.

173. The three-dimensional network of embodiment 149, wherein the oligonucleotide is 20 to 40 nucleotides long.

174. The three-dimensional network of embodiment 149, wherein the oligonucleotide is 40 to 60 nucleotides long.

175. The three-dimensional network of embodiment 149, wherein the oligonucleotide is 60 to 80 nucleotides long.

176. The three-dimensional network of embodiment 149, wherein the oligonucleotide is 80 to 100 nucleotides long.

177. The three-dimensional network of embodiment 149, wherein the oligonucleotide is 100 to 120 nucleotides long.

178. The three-dimensional network of embodiment 149, wherein the oligonucleotide is 12 to 150 nucleotides long.

179. An array comprising a plurality of three-dimensional networks according to any one of embodiments 1 to 178 on a substrate.

180. The array of embodiment 179, wherein the three-dimensional networks are immobilized on the substrate.

181. The array of embodiment 180, wherein the three-dimensional networks are immobilized on the substrate by covalent bonds between the networks and the substrate.

182. The array of any one of embodiments 179 to 181, wherein the substrate comprises an organic polymer or an inorganic material having a self-assembled monolayer of organic molecules on a surface of the inorganic material.

183. The array of embodiment 182, wherein the substrate comprises an organic polymer selected from cycloolefin copolymers, polystyrene, polyethylene, polypropylene and polymethylmethacrylate.

184. The array of embodiment 183, wherein the substrate comprises a cycloolefin copolymer, polystyrene or polymethylmethacrylate.

185. The array of embodiment 182, wherein the substrate comprises an inorganic material having an alkyl silane self-assembled monolayer on a surface of the inorganic material.

186. The array of any one of embodiments 179 to 185 which comprises at least 8 three-dimensional networks.

187. The array of any one of embodiments 179 to 185 which comprises at least 16 three-dimensional networks.

188. The array of any one of embodiments 179 to 185 which comprises at least 24 three-dimensional networks.

189. The array of any one of embodiments 179 to 185 which comprises at least 48 three-dimensional networks.

190. The array of any one of embodiments 179 to 185 which comprises at least 96 three-dimensional networks.

191. The array of any one of embodiments 179 to 185 which comprises at least 128 three-dimensional networks.

192. The array of any one of embodiments 179 to 185 which comprises at least 256 three-dimensional networks.

193. The array of any one of embodiments 179 to 185 which comprises at least 512 three-dimensional networks.

194. The array of any one of embodiments 179 to 185 which comprises at least 1024 three-dimensional networks.

195. The array of any one of embodiments 179 to 185 which comprises 24 to 8192 three-dimensional networks.

196. The array of any one of embodiments 179 to 185 which comprises 24 to 4096 three-dimensional networks.

197. The array of any one of embodiments 179 to 185 which comprises 24 to 2048 three-dimensional networks.

198. The array of any one of embodiments 179 to 185 which comprises 24 to 1024 three-dimensional networks.

199. The array of any one of embodiments 179 to 185 which comprises 24 three-dimensional networks.

200. The array of any one of embodiments 179 to 185 which comprises 48 three-dimensional networks.

201. The array of any one of embodiments 179 to 185 which comprises 96 three-dimensional networks.

202. The array of any one of embodiments 179 to 185 which comprises 128 three-dimensional networks.

203. The array of any one of embodiments 179 to 185 which comprises 256 three-dimensional networks.

204. The array of any one of embodiments 179 to 185 which comprises 512 three-dimensional networks.

205. The array of any one of embodiments 179 to 185 which comprises 1024 three-dimensional networks.

206. The array of any one of embodiments 179 to 205, wherein each of the three-dimensional networks is located at a separate spot on the substrate.

207. The array of embodiment 206, wherein the spots are arranged in columns and/or rows.

208. The array of any one of embodiments 179 to 207, wherein the substrate comprises a microwell plate and the three-dimensional networks are positioned in the wells of the plate.

209. The array of any one of embodiments 179 to 208, wherein the plurality of three-dimensional networks comprises two or more three-dimensional networks comprising different species of probe molecules.

210. The array of any one of embodiments 179 to 209, wherein the plurality of three-dimensional networks comprises two or more three-dimensional networks comprising the same species of probe molecules.

211. The array of any one of embodiments 179 to 210, wherein a majority of the three-dimensional networks comprise the same species of probe molecules or wherein all the three-dimensional networks comprises the same species of probe molecules.

212. The array of any one of embodiments 179 to 211, wherein the plurality of three-dimensional networks comprises one or more three-dimensional networks comprising labeled control probe molecules.

213. The array of embodiment 212, wherein the labeled control probe molecules are fluorescently labeled.

214. The array of embodiment 212 or embodiment 213, wherein at least one control probe molecule is a spatial control.

215. The array of any one of embodiments 179 to 214, which can be reused.

216. The array of embodiment 215, which can be reused at least 5 times.

217. The array of embodiment 215, which can be reused at least 10 times.

218. The array of embodiment 215, which can be reused at least 20 times.

219. The array of embodiment 215, which can be reused at least 30 times

220. The array of embodiment 215, which can be reused at least 40 times.

221. The array of embodiment 215, which can be reused at least 50 times.

222. The array of embodiment 215, which can be reused at least 60 times.

223. The array of embodiment 215, which can be reused at least 70 times

224. The array of embodiment 215, which can be reused at least 80 times.

225. The array of embodiment 215, which can be reused at least 90 times.

226. The array of embodiment 215, which can be reused at least 100 times.

227. The array of any one of embodiments 215 to 226, in which at least one three-dimensional network is a reusability control.

228. The array of embodiment 227, wherein the reusability control comprises a fluorescently labeled probe.

229. The array of embodiment 228, wherein the reusability control is also a spatial control.

230. A process for making a three-dimensional network having a surface and an interior comprising (a) a crosslinked polymer and (b) one or more channels, comprising:
   (a) exposing a mixture to salt crystal forming conditions, said mixture comprising (i) an aqueous salt solution, (ii) a polymer, and (iii) a cross-linker and optionally positioned on the surface of a substrate, thereby forming a mixture containing one or more salt crystals;
   (b) exposing the mixture containing one or more salt crystals to crosslinking conditions, thereby forming a crosslinked polymer network containing one or more salt crystals; and
   (c) contacting the crosslinked polymer network containing one or more salt crystals with a solvent in which the one or more salt crystals are soluble, thereby dissolving the salt crystals and forming one or more channels in place of the salt crystals; thereby forming the three-dimensional network comprising a crosslinked polymer and one or more channels.

231. The process of embodiment 230, wherein the salt forming conditions comprise forming one or more needle-shaped crystals.

232. The process of embodiment 230 or embodiment 231, in which at least one of the one or more channels has the properties of the channels of the networks of any one of embodiments 2 to 51.

233. The process of embodiment 230 or embodiment 231, in which a three-dimensional network having a surface and an interior comprising (a) a crosslinked polymer and (b) a plurality of channels is produced.

234. The process of embodiment 233, in which the plurality of channels have the properties of the plurality of channels of the networks of any one of embodiments 53 to 112.

235. The process of any one of embodiments 230 to 234, wherein the salt forming conditions comprise dehydrating the mixture.

236. The process of embodiment 235, which comprises dehydrating the mixture by heating the mixture, exposing the mixture to a vacuum, reducing the humidity of the atmosphere surrounding the mixture, or a combination thereof.

237. The process of embodiment 236, which comprises dehydrating the mixture by exposing the mixture to a vacuum.

238. The process of embodiment 236, which comprises dehydrating the mixture by heating the mixture.

239. The process of embodiment 238, wherein heating the mixture comprises contacting the mixture with a gas that has a temperature which is higher than the temperature of the mixture.

240. The process of any one of embodiments 230 to 234, wherein the salt forming conditions comprise cooling the mixture until the mixture becomes supersaturated with the salt.

241. The process of embodiment 240, which comprises cooling the mixture by contacting the mixture with a gas that has a temperature which is lower than the temperature of the mixture.

242. The process of any one of embodiments 230 to 241, wherein the temperature of the mixture during step (a) is maintained above the dew point of the atmosphere surrounding the mixture.

243. The process of any one of embodiments 230 to 242, wherein the cross-linker is activated by ultraviolet (UV) light and the crosslinking conditions comprise exposing the mixture to ultraviolet light.

244. The process of any one of embodiments 230 to 242, wherein the cross-linker is activated by visible light and the crosslinking conditions comprise exposing the mixture to visible light.

245. The process of any one of embodiments 230 to 242, wherein the cross-linker is activated by heat and the crosslinking conditions comprise exposing the mixture to heat.

246. The process of any one of embodiments 230 to 245, wherein the aqueous salt solution comprises monovalent cations.

247. The process of embodiment 246, in which the monovalent cations comprise $Na^+$ and/or $K^+$, preferably wherein the monovalent cations comprise $Na^+$ and $K^+$.

248. The process of embodiment 247, wherein the aqueous salt solution comprises a solution produced by a process comprising dissolving disodium hydrogen phosphate, sodium dihydrogen phosphate, dipotassium hydrogen phosphate, potassium dihydrogen phosphate, or a combination thereof in water or an aqueous solution.

249. The process of any one of embodiments 230 to 248, wherein the polymer is a water-soluble polymer.

250. The process of any one of embodiments 230 to 249, wherein the polymer comprises a homopolymer.

251. The process of any one of embodiments 230 to 249, wherein the polymer comprises a copolymer.

252. The process of any one of embodiments 230 to 249, wherein the polymer comprises a mixture of a homopolymer and a copolymer.

253. The process of any one of embodiments 249 to 252, wherein the polymer comprises a polymer polymerized from one or more species of monomers.

254. The process of embodiment 253, wherein each species of monomer comprises a polymerizable group independently selected from an acrylate group, a methacrylate group, an ethacrylate group, a 2-phenyl acrylate group, an acrylamide group, a methacrylamide group, an itaconate group, and a styrene group.

255. The process of embodiment 254, wherein at least one monomer species in the polymer comprises a methacrylate group.

256. The process of embodiment 255, wherein the at least one monomer species comprising a methacrylate group is methacryloyloxybenzophenone (MABP).

257. The process of any one of embodiment 253, wherein the polymer comprises a polymer polymerized from dimethylacrylamide (DMAA), methacryloyloxybenzophenone (MABP), and sodium 4-vinylbenzenesulfonate (SSNa).

258. The process of any one of embodiments 230 to 257, wherein the polymer is a copolymer comprising the cross-linker.

259. The process of embodiment 258, wherein the polymer comprises at least two cross-linkers per polymer molecule.

260. The process of any one of embodiments 230 to 259, wherein the cross-linker is selected from benzophenone, a thioxanthone, a benzoin ether, ethyl eosin, eosin Y, rose bengal, camphorquinone, erythirosin, 4,4' azobis(4-cyanopentanoic) acid, 2,2-azobis[2-(2-imidazolin-2-yl) propane] dihydrochloride, and benzoyl peroxide.

261. The process of claim 260, wherein the cross-linker is benzophenone.

262. The process of any one of embodiments 230 to 261, wherein the solvent is water or a water-based buffer.

263. The process of embodiment 262, wherein the solvent is water.

264. The process of embodiment 262, wherein the solvent is a water-based buffer.

265. The process of embodiment 264, wherein the water-based buffer comprises phosphate, methanol, ethanol, propanol, or a mixture thereof.

266. The process of any one of embodiments 230 to 265, wherein the mixture of step (a) further comprises probe molecules.

267. The process of embodiment 266, wherein at least some, the majority or all the probe molecules comprise a nucleic acid, a nucleic acid derivative, a peptide, a polypeptide, a protein, a carbohydrate, a lipid, a cell, a ligand, or a combination thereof.

268. The process of embodiment 267, wherein at least some of the probe molecules comprise a nucleic acid or a nucleic acid derivative.

269. The process of embodiment 267, wherein at least a majority of the probe molecules comprise a nucleic acid or a nucleic acid derivative.

270. The process of embodiment 267, wherein all the probe molecules comprise a nucleic acid or a nucleic acid derivative.

271. The process of embodiment 266, wherein at least some, the majority or all the probe molecules comprise an antibody, an antibody fragment, an antigen, an epitope, an enzyme, an enzyme substrate, an enzyme inhibitor, a nucleic acid, or a combination thereof.

272. The process of embodiment 271, wherein at least some of the probe molecules comprise a nucleic acid.

273. The process of embodiment 271, wherein at least a majority of the probe molecules comprise a nucleic acid.

274. The process of embodiment 271, wherein all the probe molecules comprise a nucleic acid.

275. The process of any one of embodiments 272 to 274, wherein the nucleic acid is an oligonucleotide.

276. The process of embodiment 275, wherein the oligonucleotide is 12 to 30 nucleotides long.

277. The process of embodiment 275, wherein the oligonucleotide is 14 to 30 nucleotides long.

278. The process of embodiment 275, wherein the oligonucleotide is 14 to 25 nucleotides long.

279. The process of embodiment 275, wherein the oligonucleotide is 14 to 20 nucleotides long.

280. The process of embodiment 275, wherein the oligonucleotide is 15 to 30 nucleotides long.

281. The process of embodiment 275, wherein the oligonucleotide is 15 to 25 nucleotides long.

282. The process of embodiment 275, wherein the oligonucleotide is 15 to 20 nucleotides long.

283. The process of embodiment 275, wherein the oligonucleotide is 16 to 30 nucleotides long.

284. The process of embodiment 275, wherein the oligonucleotide is 16 to 25 nucleotides long.

285. The process of embodiment 275, wherein the oligonucleotide is 16 to 20 nucleotides long.

286. The process of embodiment 275, wherein the oligonucleotide is 15 to 40 nucleotides long.

287. The process of embodiment 275, wherein the oligonucleotide is 15 to 45 nucleotides long.

288. The process of embodiment 275, wherein the oligonucleotide is 15 to 50 nucleotides long.

289. The process of embodiment 275, wherein the oligonucleotide is 15 to 60 nucleotides long.

290. The process of embodiment 275, wherein the oligonucleotide is 20 to 55 nucleotides long.

291. The process of embodiment 275, wherein the oligonucleotide is 18 to 60 nucleotides long.

292. The process of embodiment 275, wherein the oligonucleotide is 20 to 50 nucleotides long.

293. The process of embodiment 275, wherein the oligonucleotide is 30 to 90 nucleotides long.

294. The process of embodiment 275, wherein the oligonucleotide is 20 to 100 nucleotides long.

295. The process of embodiment 275, wherein the oligonucleotide is 20 to 120 nucleotides long.

296. The process of embodiment 275, wherein the oligonucleotide is 20 to 40 nucleotides long.

297. The process of embodiment 275, wherein the oligonucleotide is 20 to 60 nucleotides long.

298. The process of embodiment 275, wherein the oligonucleotide is 40 to 80 nucleotides long.

299. The process of embodiment 275, wherein the oligonucleotide is 40 to 100 nucleotides long.

300. The process of embodiment 275, wherein the oligonucleotide is 40 to 60 nucleotides long.

301. The process of embodiment 275, wherein the oligonucleotide is 60 to 80 nucleotides long.

302. The process of embodiment 275, wherein the oligonucleotide is 80 to 100 nucleotides long.

303. The process of embodiment 275, wherein the oligonucleotide is 100 to 120 nucleotides long.

304. The process of embodiment 275, wherein the oligonucleotide is 12 to 150 nucleotides long.

305. The process of any one of embodiments 230 to 304, further comprising, prior to step (a), a step of applying the mixture to a surface of a substrate.

306. The process of embodiment 305, wherein the mixture is applied in a volume of in a volume of 100 pl to 5 nl.

307. The process of embodiment 305, wherein the mixture is applied in a volume of in a volume of 100 pl to 1 nl.

308. The process of embodiment 305, wherein the mixture is applied in a volume of in a volume of 200 pl to 1 nl.

309. The process of any one of embodiments 305 to 308, wherein the step of applying the mixture to the substrate comprises spraying the mixture onto the surface of the substrate.

310. The process of embodiment 309, wherein the mixture is sprayed by an inkjet printer.

311. The process of any one of embodiments 305 to 310, wherein the substrate comprises an organic polymer or an inorganic material having a self-assembled monolayer of organic molecules on the surface.

312. The process of embodiment 311, wherein the substrate comprises an organic polymer.

313. The process of embodiment 312, wherein the organic polymer is selected from cycloolefin copolymers, polystyrene, polyethylene, polypropylene and polymethylmethacrylate.

314. The process of embodiment 313, wherein the substrate comprises polymethylmethacrylate, polystyrene, or cycloolefin copolymers.

315. The process of embodiment 311, wherein the substrate comprises an inorganic material having an alkyl silane self-assembled monolayer on the surface.

316. The process of any one of embodiments 305 to 315, wherein the substrate comprises a microwell plate.

317. The process of any one of embodiments 305 to 316, wherein the polymer is crosslinked to the surface in step (b).

318. The process of embodiment 317, in which a water-swellable polymer is produced that is crosslinked to the surface.

319. The process of embodiment 318, wherein the water-swellable polymer can absorb up to 50 times its weight of deionized, distilled water.

320. The process of embodiment 318 or embodiment 319, wherein the water-swellable polymer can absorb 5 to 50 times its own volume of deionized, distilled water.

321. The process of any one of embodiments 318 to 320, wherein the water-swellable polymer can absorb up to 30 times its weight of saline.

322. The process of any one of embodiments 318 to 321, wherein the water-swellable polymer can absorb 4 to 30 times its own volume of saline.

323. A process for making an array, comprising generating a plurality of three-dimensional networks by the process of any one of claims 230 to 322 at discrete spots on the surface of the same substrate.

324. The process of embodiment 323, wherein the three-dimensional networks are generated simultaneously.

325. The process of embodiment 323, wherein the three-dimensional networks are generated sequentially.

326. The process of any one of embodiments 323 to 325, further comprising crosslinking the plurality of three-dimensional networks to the surface of the substrate.

327. A process for making an array, comprising positioning a plurality of three-dimensional networks (a) according to any one of embodiments 1 to 178 or (b) produced or obtainable according to the process of any one of embodiments 230 to 322 at discrete spots on a surface of the same substrate.

328. The process of any one of embodiments 323 to 327, further comprising crosslinking the plurality of three-dimensional networks to the surface.

329. A process for making an array, comprising positioning a plurality of three-dimensional networks produced or obtainable according to the process of any one of embodiments 305 to 322 at discrete spots on a surface of the same substrate.

330. The process of embodiment 329, wherein the positioning comprises applying the mixtures from which the three-dimensional networks are formed at the discrete spots.

331. The process of any one of embodiments 323 to 330, wherein the spots are arranged in columns and/or rows.

332. A three-dimensional network produced or obtainable by the process of any one of embodiments 230 to 322.

333. An array comprising a plurality of three-dimensional networks according to embodiment 332 on a substrate.

334. An array produced or obtainable by the process of any one of embodiments 323 to 331.

335. The array of embodiment 333 or embodiment 334 which comprises at least 8 three-dimensional networks.

336. The array of embodiment 333 or embodiment 334 which comprises at least 16 three-dimensional networks.

337. The array of embodiment 333 or embodiment 334 which comprises at least 24 three-dimensional networks.

338. The array of embodiment 333 or embodiment 334 which comprises at least 48 three-dimensional networks.

339. The array of embodiment 333 or embodiment 334 which comprises at least 96 three-dimensional networks.

340. The array of embodiment 333 or embodiment 334 which comprises at least 128 three-dimensional networks.

341. The array of embodiment 333 or embodiment 334 which comprises at least 256 three-dimensional networks.

342. The array of embodiment 333 or embodiment 334 which comprises at least 512 three-dimensional networks.

343. The array of embodiment 333 or embodiment 334 which comprises at least 1024 three-dimensional networks.

344. The array of embodiment 333 or embodiment 334 which comprises 24 to 8192 three-dimensional networks.

345. The array of embodiment 333 or embodiment 334 which comprises 24 to 4096 three-dimensional networks.

346. The array of embodiment 333 or embodiment 334 which comprises 24 to 2048 three-dimensional networks.

347. The array of embodiment 333 or embodiment 334 which comprises 24 to 1024 three-dimensional networks.

348. The array of embodiment 333 or embodiment 334 which comprises 24 three-dimensional networks.

349. The array of embodiment 333 or embodiment 334 which comprises 48 three-dimensional networks.

350. The array of embodiment 333 or embodiment 334 which comprises 96 three-dimensional networks.

351. The array of embodiment 333 or embodiment 334 which comprises 128 three-dimensional networks.

352. The array of embodiment 333 or embodiment 334 which comprises 256 three-dimensional networks.

353. The array of embodiment 333 or embodiment 334 which comprises 512 three-dimensional networks.

354. The array of embodiment 333 or embodiment 334 which comprises 1024 three-dimensional networks.

355. The array of any one of embodiments 333 to 354, wherein the three-dimensional networks comprise probe molecules, and two or more of three-dimensional networks comprise different species of probe molecules.

356. The array of any one of embodiments 333 to 355, wherein the three-dimensional networks comprise probe molecules, and two or more three-dimensional networks comprise the same species of probe molecules.

357. The array of any one of embodiments 333 to 354, wherein the three-dimensional networks comprise probe molecules, and each of the three-dimensional networks comprise the same species of probe molecules.

358. The array of any one of embodiments 333 to 357, wherein the plurality of three-dimensional networks comprises one or more three-dimensional networks comprising labeled control probe molecules.

359. The array of embodiment 358, wherein the labeled control probe molecules are fluorescently labeled.

360. The array of any one of embodiments 333 to 359, wherein the substrate comprises a microwell plate and each well of the microwell plate contains no more than a single three-dimensional network.

361. A method for determining whether an analyte is present in a sample, comprising:
(a) contacting a three-dimensional network according to any one of embodiments 1 to 178 or 332 or an array of any one of embodiments 179 to 229 or 333 to 360 comprising probe molecules that are capable of binding to the analyte with the sample; and
(b) detecting binding of the analyte to the probe molecules in the three-dimensional network or array, thereby determining whether the analyte is present in the sample.

362. The method of embodiment 361, which further comprises washing the network or array comprising probe molecules between steps (a) and (b).

363. The method of embodiment 361 or embodiment 362, which further comprises contacting the network or array comprising probe molecules with a blocking reagent prior to step (a).

364. The method of any one of embodiments 361 to 363, further comprising quantifying the amount of analyte bound to the three-dimensional network or array comprising probe molecules.

365. A method for determining whether an analyte is present in each sample in a plurality of samples, comprising:
  (a) contacting an array of any one of embodiments 179 to 229 or 333 to 360 comprising probe molecules that are capable of binding to the analyte with the samples; and
  (b) detecting binding of the analyte to the probe molecules in the array, thereby determining whether the analyte is present in each sample in the plurality of samples.

366. A method for determining whether an analyte is present in each sample in a plurality of samples, comprising:
  (a) contacting an array of any one of embodiments 179 to 229 or 333 to 360 comprising probe molecules that are capable of binding to the analyte with the samples and comprising control probe molecules, wherein the array has been used and washed prior to step (a); and
  (b) detecting binding of the analyte to the probe molecules in the array, thereby determining whether the analyte is present in each sample in the plurality of samples.

367. A method for determining whether more than one species of analyte is present in a sample, comprising:
  (a) contacting an array of any one of embodiments 179 to 229 or 333 to 360 comprising different species of probe molecules that are capable of binding to the different species of analytes with the sample; and
  (b) detecting binding of the analytes to the probe molecules in the array, thereby determining whether more than one species of analyte are present in the sample.

368. A method for determining whether more than one species of analyte is present in a sample, comprising:
  (a) contacting an array of any one of embodiments 179 to 229 or 333 to 360 comprising different species of probe molecules that are capable of binding to the different species of analytes with the sample and comprising control probe molecules, wherein the array has been used and washed prior to step (a); and
  (b) detecting binding of the analytes to the probe molecules in the array, thereby determining whether more than one species of analyte are present in the sample.

369. The method of any one of embodiments 365 to 368, in which:
  (a) the substrate of the array comprises a microwell plate;
  (b) each well of the microwell plate contains no more than a single three-dimensional network; and
  (c) contacting the array with the samples comprises contacting each well with no more than a single sample.

370. The method of any one of embodiments 365 to 369, which further comprises washing the array comprising probe molecules between steps (a) and (b).

371. The method of any one of embodiments 365 to 370, which further comprises contacting the array comprising probe molecules with a blocking reagent prior to step (a).

372. The method of any one of embodiments 365 to 371, further comprising quantifying the amount of analyte or analytes bound to the array.

373. The method of any one of embodiments 361 to 372, further comprising reusing the array.

374. The method of embodiment 373, wherein the array is reused at least 5 times.

375. The method of embodiment 373, wherein the array is reused at least 10 times.

376. The method of embodiment 373, wherein the array is reused at least 20 times.

377. The method of embodiment 373, wherein the array is reused at least 30 times.

378. The method of embodiment 373, wherein the array is reused at least 40 times.

379. The method of embodiment 373, wherein the array is reused at least 50 times.

380. The method of embodiment 374, which comprises reusing the array 5 to 20 times.

381. The method of embodiment 374, which comprises reusing the array 5 to 30 times.

382. The method of embodiment 374, which comprises reusing the array 10 to 50 times.

383. The method of embodiment 374, which comprises reusing the array 10 to 20 times.

384. The method of embodiment 374, which comprises reusing the array 10 to 30 times.

385. The method of embodiment 374, which comprises reusing the array 20 to 40 times.

386. The method of embodiment 374, which comprises reusing the array 40 to 50 times.

387. The method of any one of embodiments 373 to 386, which comprises washing the array between reuses.

388. The method of embodiment 387, wherein the array is washed under denaturing conditions.

389. The method of embodiment 388 wherein the denaturing conditions comprise exposing the array to heat.

390. The method of embodiment 388 wherein the denaturing conditions comprise exposing the array to low salt concentrations.

391. The method of embodiment 388 wherein the denaturing conditions comprise exposing the array to both heat and low salt concentrations.

392. The method of embodiment 388, wherein the denaturing conditions are removed prior to reuse.

393. The method of embodiment 392, wherein the denaturing conditions comprise exposing the array to heat and wherein the temperature is lowered prior to reuse.

394. The method of embodiment 392, wherein the denaturing conditions comprise exposing the array to low salt concentrations and wherein the salt concentration is increased prior to reuse.

395. The method of embodiment 392, wherein the denaturing conditions comprise exposing the array to both heat and low salt concentrations and wherein the temperature is lowered and the salt concentration is increased prior to reuse.

396. The method of any one of embodiments 373 to 395, wherein the array comprises at least one three-dimensional network comprising a fluorescently labelled oligonucleotide as a reusability control.

397. The method of embodiment 396, which comprises testing the fluorescent signal strength.

398. The method of embodiment 397, wherein the reusability control retains at least 70% of its initial fluorescence signal strength after 10 uses.

399. The method of embodiment 398, wherein the reusability control retains at least 50% of its signal strength after 20 uses.

400. The method of any one of embodiments 396 to 399, wherein the array is no longer reused after the reusability control loses more than 50% of its signal strength.

401. The method of any one of embodiments 361 to 400, wherein analyte is a nucleic acid.

402. The method of embodiment 401, wherein the nucleic acid is a polymerase chain reaction (PCR) amplicon.

403. The method of embodiment 401, wherein the PCR amplicon is amplified from a biological sample or environmental sample.

404. The method of embodiment 403, wherein the PCR amplicon is amplified from a biological sample.

405. The method of embodiment 403, wherein the PCR amplicon is amplified from an environmental sample.

406. The method of embodiment 404, wherein the biological sample is a blood, serum, plasma, tissue, cells, saliva, sputum, urine, cerebrospinal fluid, pleural fluid, milk, tears, stool, sweat, semen, whole cells, cell constituent, cell smear, or an extract or derivative thereof.

407. The method of embodiment 406, wherein the biological sample is mammalian blood, serum or plasma or an extract thereof.

408. The method of embodiment 407, wherein the biological sample is human or bovine blood, serum or plasma or an extract thereof.

409. The method of embodiment 406, wherein the biological sample is milk or an extract thereof.

410. The method of embodiment 409, wherein the biological sample is cow's milk or an extract thereof.

411. The method of any one of embodiments 401 to 410, wherein nucleic acid is labeled.

412. The method of embodiment 411, wherein the nucleic acid is fluorescently labeled.

413. A three-dimensional network (15) having a surface (16) and an interior comprising:
  (a) a crosslinked polymer (3) covalently attached to the surface (2) of a substrate;
  (b) one or more channels (13); and
  (c) probe molecules immobilized (1) in the network (15), optionally wherein
    (i) probe molecules (1) are covalently attached to the network (15) and/or
    (ii) a majority of probe molecules (1) are immobilized in the interior of the network (15) and/or
    (iii) a majority of probe molecules (1) adjoin a channel (13).

414. The three-dimensional network (15) of embodiment 413, wherein at least one or at least a majority of the channels (13) is characterized by one, two, or three of the following properties:
  (a) the channel (13) extends into the interior from a point that is less than 5 microns from the surface (16) of the network (15) or extends into the interior from a point on the surface (16) of the network (15);
  (b) the channel (13) has a length that is at least 10 or at least 20% of the largest dimension of the network (15); and
  (c) the channel (13) has a minimum cross-section of at least 5 times or at least 15 times the network's (15) mesh size.

415. The three-dimensional network (15) of embodiment 414, wherein at least one or at least a majority of the channels (13)
  (a) has a length that is 10% to 40% or 15% to 25% of the largest dimension of the network (15) and/or
  (b) has a minimum cross-section of 5 to 10 times or 10 to 25 times the network's (15) mesh size.

416. The three-dimensional network (15) of any one of embodiments 413 to 415, comprising at least 5 channels (13), at least 10 channels (13) or at least 15 channels (13), optionally wherein a plurality of channels (13) converge at a point in the interior of the network (15) such that the lateral distance between the channels (13) decreases from the surface (16) of the network (15) toward the point in the interior, and optionally wherein each channel (13) is independently characterized by one, two, or three of the following properties:
  (a) the channel (13) extends into the interior from a point that is less than 10 microns, less than 9 microns, less than 8 microns, less than 7 microns, less than 6 microns, less than 5 microns, less than 4 microns, less than 3 microns, less than 2 microns, less than 1 micron from the surface (16) of the network (15) or on the surface (16) of the network (15);
  (b) the channel (13) has a length that is at least 10%, at least 15%, at least 20%, or at least 25% of the largest dimension of the network (15), and; and/or
  (c) the channel (13) has a minimum cross-section of at least 5 times, at least 10 times, at least 15 times, or at least 20 times the network's (15) mesh size.

417. The three-dimensional network (15) of any one of embodiments 413 to 416, wherein the network (15) has in its hydrated state a mesh size of 5 to 75 nm or 10 to 50 nm.

418. An array comprising a plurality of three-dimensional networks (15) according to any one of embodiments 413 to 417 on a substrate, optionally wherein (a) the three-dimensional networks (15) are immobilized on the substrate and/or (b) each of the three-dimensional networks (15) is located at a separate spot (7) on the substrate.

419. The array of embodiment 418, comprising at least 8 or at least 48 three-dimensional networks (15), optionally wherein the number of three-dimensional networks (15) on the array ranges between 24 and 1024.

420. The array of embodiment 418 or embodiment 419, wherein the plurality of three-dimensional networks (15) comprises one or more three-dimensional networks (15) comprising labeled control probe molecules (1), optionally wherein the labeled control probe molecules (1) are fluorescently labeled.

421. The array of any one of embodiments 418 to 420 which can be reused, optionally wherein the array can be reused at least 10 times.

422. A process for making a three-dimensional network (15) according to any one of embodiments 413 to 417, comprising the steps of:
  (a) exposing a mixture (5) positioned on the surface (2) of a substrate to needle-shaped crystal forming conditions, said mixture (5) comprising
    (i) an aqueous salt solution which is optionally a monovalent cation salt solution,
    (ii) a polymer, and (iii) a cross-linker, thereby forming a mixture (5) containing one or more needle-shaped salt crystals (8);
  (b) exposing the mixture (5) containing one or more salt crystals (8) to crosslinking conditions, thereby forming a crosslinked polymer network (15) containing one or more needle-shaped salt crystals (8); and
  (c) contacting the crosslinked polymer network (15) containing one or more salt crystals (8) with a solvent in which the one or more salt crystals (8) are soluble, thereby dissolving the needle-shaped salt crystals (8) and forming one or more channels (13) in place of the salt crystals (8).

423. The process of embodiment 422, wherein:
(a) the needle-shaped crystal salt forming conditions comprise:
   (i) dehydrating the mixture (5) optionally by heating the mixture (5) (optionally by contacting the mixture (5) with a gas that has a temperature which is higher than the temperature of the mixture (5)), exposing the mixture (5) to a vacuum, and/or reducing the humidity of the atmosphere surrounding the mixture (5); or
   (ii) cooling the mixture (5), optionally by contacting the mixture (5) with a gas that has a temperature which is lower than the temperature of the mixture (5); and/or
(b) wherein the solvent is a water-based buffer, said buffer optionally comprising phosphate, methanol, ethanol, propanol, or a mixture thereof.

424. The process of embodiment 422 or embodiment 423, wherein the mixture (5) of step (a) further comprises probe molecules (1).

425. The process of any one of embodiments 422 to 424, further comprising, prior to step (a), a step of applying the mixture (5) to a surface (2) of a substrate, optionally in a volume of 100 pl to 5 nl, in a volume of 100 pl to 1 nl or in a volume 500 pl to 2 nl.

426. A process for making an array, comprising (a) creating a plurality of three-dimensional networks (15) by the process of any one of embodiments 422 to 425 at discrete spots (7) on the surface (2) of the same substrate, and (b) crosslinking the plurality of three-dimensional networks (15) to the surface (2) of the substrate.

427. A method for determining whether an analyte is present in a sample, comprising:
(a) contacting a three-dimensional network (15) according to any one of embodiments 413 to 417 comprising probe (1) molecules that are capable of binding to the analyte with the sample, optionally wherein the three-dimensional network (15) is positioned on an array according to any one of embodiments 418 to 421; and
(b) detecting and optionally quantifying binding of the analyte to the probe molecules (1) in the three-dimensional network (15) or array, thereby determining whether the analyte is present in the sample and optionally the amount of the analyte.

428. The method of embodiment 427, wherein:
(a) the network (15) or array has been used and washed prior to step (a), optionally at least 10 times, at least 20 times or at least 50 times; and/or
(b) further comprising reusing the network (15) or array following step (b), optionally at least 10 times, at least 20 times or at least 50 times.

429. The method of embodiment 427 or embodiment 428, wherein the analyte is a nucleic acid, optionally wherein the nucleic acid is a fluorescently labeled polymerase chain reaction (PCR) amplicon.

While various specific embodiments have been illustrated and described, it will be appreciated that various changes can be made without departing from the spirit and scope of the disclosure(s).

10. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

The invention claimed is:

1. A three-dimensional network having a surface and an interior, said three-dimensional network:
(a) is composed of a water-swellable polymer of cross-linked water-soluble polymer chains;
(b) is crosslinked to the surface of a substrate;
(c) comprises multiple pluralities of channels, wherein:
   (i) each plurality of channels comprises channels that converge at a point in the interior of the network such that the lateral distance between the channels decreases from the surface of the network toward the point in the interior; and
   (ii) each plurality of channels converges at a different point in the three-dimensional network; and
(d) comprises probe molecules covalently attached to the polymer chains.

2. The three-dimensional network of claim 1, wherein a majority of probe molecules are in the interior of the three-dimensional network and/or adjoin a channel.

3. The three-dimensional network of claim 1, wherein the polymer comprises a polymer polymerized from dimethyl-acrylamide (DMAA), methacryloyloxybenzophenone (MABP), and sodium 4-vinylbenzenesulfonate (SSNa).

4. An array comprising a plurality of three-dimensional networks according to claim 1, wherein each of the three-dimensional networks is located at a separate spot on the substrate.

5. The array of claim 4, which can be reused at least 10 times.

6. A process for making a three-dimensional network, comprising the steps of:
(a) applying a mixture comprising (i) an aqueous salt solution which is optionally a monovalent cation salt solution, (ii) a water-soluble polymer, (iii) a cross-linker, and (iv) probe molecules to a substrate in a volume of 100 pl to 5 nl;
(b) exposing the mixture to needle-shaped crystal forming conditions, thereby forming a mixture containing one or more needle-shaped salt crystals;
(c) exposing the mixture containing the needle-shaped salt crystals to crosslinking conditions, thereby forming a crosslinked polymer network having probe molecules crosslinked thereto and containing needle-shaped salt crystals; and
(d) contacting the crosslinked polymer network containing the needle-shaped salt crystals with a solvent in which the needle-shaped salt crystals are soluble, thereby dissolving the needle-shaped salt crystals and forming channels in place of the needle-shaped salt crystals.

7. The process of claim 6, wherein:
(a) the solvent is a water-based buffer; and/or;
(b) the needle-shaped crystal salt forming conditions comprise:
   (i) dehydrating the mixture; or
   (ii) cooling the mixture.

8. A process for making an array, comprising (a) creating a plurality of three-dimensional networks by the process of claim 6 at discrete spots on the surface of the substrate, and (b) crosslinking the plurality of three-dimensional networks to the surface.

9. A method for determining whether an analyte is present in a sample, comprising:
(a) contacting a three-dimensional network according to claim 1 comprising probe molecules that are capable of binding to the analyte with the sample; and
(b) detecting binding of the analyte to the probe molecules in the three-dimensional network, thereby determining whether the analyte is present in the sample and optionally the amount of the analyte.

10. The method of claim 9, wherein the three-dimensional network has been used and washed at least 10 times prior to (a) or which further comprises reusing the three-dimensional network at least 10 times following (b).

11. The method of claim 10, which further comprises quantifying binding of the analyte to the probe molecules in the three-dimensional network.

12. The three-dimensional network of claim 1, wherein the three-dimensional network comprises two to ten pluralities of channels, each plurality converging at a different point within the three-dimensional network.

13. The three-dimensional network of claim 1, wherein the three-dimensional network comprises two pluralities of channels, each plurality converging at a different point within the three-dimensional network.

14. The three-dimensional network of claim 1, wherein the probe molecules comprise nucleic acids.

15. The three-dimensional network of claim 14, wherein the nucleic acids are oligonucleotides.

16. The array of claim 4, wherein the plurality of three-dimensional networks comprises two or more three-dimensional networks comprising different species of probe molecules.

17. The array of claim 4, wherein the plurality of three-dimensional networks comprises one or more three-dimensional networks comprising labeled control probe molecules.

18. The array of claim 17, wherein the labeled control probe molecules are fluorescently labeled.

19. The array of claim 17, wherein at least one control probe molecule is a spatial control probe.

20. The array of claim 17, wherein at least one control probe molecule is a reusability control probe.

21. The array of claim 20, wherein the reusability control probe is also a spatial control probe.

* * * * *